United States Patent
Atkins et al.

(10) Patent No.: US 11,472,783 B2
(45) Date of Patent: Oct. 18, 2022

(54) PROCESS FOR THE PREPARATION OF GLYCIDOL

(71) Applicant: Green Lizard Technologies Ltd, Belfast (IE)

(72) Inventors: Martin Atkins, Belfast (IE); Fergal Coleman, Belfast (IE); Sean Hardiman, Belfast (IE)

(73) Assignee: Green Lizard Technologies Ltd., Belfast (IE)

( * ) Notice: Subject to any disclaimer, the term of this patent is extended or adjusted under 35 U.S.C. 154(b) by 191 days.

(21) Appl. No.: 17/042,309

(22) PCT Filed: Mar. 28, 2019

(86) PCT No.: PCT/GB2019/050904
§ 371 (c)(1),
(2) Date: Sep. 28, 2020

(87) PCT Pub. No.: WO2019/186180
PCT Pub. Date: Oct. 3, 2019

(65) Prior Publication Data
US 2021/0017142 A1 Jan. 21, 2021

(30) Foreign Application Priority Data
Mar. 28, 2018 (GB) ..................... 1805029

(51) Int. Cl.
C07D 301/02 (2006.01)
C07D 303/14 (2006.01)

(52) U.S. Cl.
CPC ......... *C07D 301/02* (2013.01); *C07D 303/14* (2013.01)

(58) Field of Classification Search
CPC ............................ C07D 301/02; C07D 303/14
USPC ....................................................... 549/519
See application file for complete search history.

(56) References Cited

U.S. PATENT DOCUMENTS

| | | | |
|---|---|---|---|
| 2,636,040 A | 4/1953 | Bruson et al. | |
| 6,316,641 B1 | 11/2001 | Yoo et al. | |
| 7,868,192 B1 * | 1/2011 | Seki ..................... | C07D 301/02 549/555 |

FOREIGN PATENT DOCUMENTS

| | | |
|---|---|---|
| JP | 2009149576 A | 7/2009 |
| JP | 2015199675 A | 11/2015 |
| WO | 9840371 A1 | 9/1998 |
| WO | 2017017307 A1 | 2/2017 |

OTHER PUBLICATIONS

W.L.Hyde and W.B Glover; "Selecting Evaporators for Process Applications"; 1997, vol. 60, pp. 59-61; CEP Magazine Dec. 2004 published by AIChE, pp. 26-33.
Sanjay B. Pawar et al.; "CFD analysis of flow pattern in the agitated thin film evaporator"; Chemical Engineering Research and Design, 2012, vol. 90 Issue 6, pp. 757-765.
Rongxian Bai et al.; "Retraction: One-pot synthesis of glycidol from glycerol and dimethyl carbonate over a highly efficient and easily available solid catalyst NaAlO2"; Green Chemistry, 2013, vol. 15, cover page only.
Choi Ji Sik et al: "Ionic-liquid-catalyzed decarboxylation of glycerol carbonate to glycidol", Journal of Catalysis, vol. 297, Nov. 17, 2012 (Nov. 17, 2012), pp. 248-255, XP028961139, ISSN: 0021-9517, DOI:10.1016/J.JCAT.2012.10.015 cited in the application entry 1 of table 1 together with paragraph 2.2; p. 249.
GB Search Report dated Dec. 24, 2018 forGB1805029.4.
Harris R F et al: "Reactions of Glycerolwith Poly (Ethylene Ether Carbonate) Polyols", Journal of Applied Polymer Science, John Wiley & Sons, Inc. US, vol. 44, No. 9, Jan. 1, 1992 (Jan. 1, 1992), pp. 1663-1670, XP001057587, ISSN: 0021-8995, DOI: 10.1002/APP.1992.070440921 right column; p. 1667, line 1-line 4 p. 1668; figure 5.
International Search Report dated May 15, 2019forApp. No. PCT/GB2019/050904.

* cited by examiner

*Primary Examiner* — Kristin A Vajda
(74) *Attorney, Agent, or Firm* — Ryan T. Grace; Advent, LLP

(57) ABSTRACT

This invention relates to a process for the preparation of glycidol from the thermal decarboxylation of glycerol carbonate. In one aspect, the present invention provides a process for the preparation of glycidol by thermal decarboxylation of glycerol carbonate, said process comprising the steps of:
 d) contacting liquid glycerol carbonate with a decarboxylation promotor, having a boiling point of at least 160° C. at atmospheric pressure and consisting essentially of an aliphatic mono-ol, an aliphatic polyol, or mixtures thereof, to form a liquid phase mixture;
 e) applying heat to the liquid phase mixture formed in step a) to induce thermal decarboxylation of the glycerol carbonate; and
 f) separating glycidol formed in step b) from the liquid phase mixture by evaporation of glycidol; and
wherein the process does not comprise the use of a decarboxylation catalyst.

22 Claims, 5 Drawing Sheets

PROCESS FOR THE PREPARATION OF GLYCIDOL

Figure 1A:
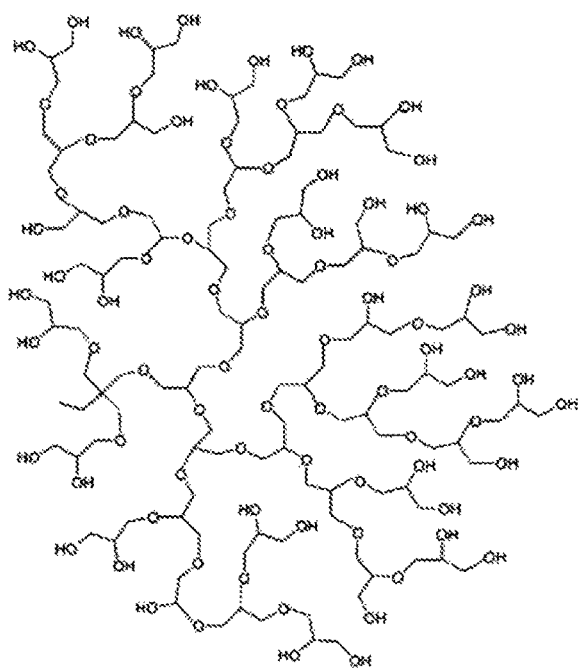

This invention relates to a process for the preparation of glycidol from the thermal decarboxylation of glycerol carbonate. More specifically, the invention relates to a process wherein liquid glycerol carbonate is contacted with a certain decarboxylation promotor, the resulting mixture is heated so as to induce thermal decarboxylation of the glycerol carbonate and product glycidol is separated from the reaction mixture by evaporation. This process achieves high conversion and selectivity for the formation of glycidol and advantageously obviates the use of a decarboxylation catalyst.

Glycidol (GLD) is a known compound which has a number of valuable industrial uses. It is known to have properties making it useful in stabilizers, plastics modifiers, surfactants, gelation agents and sterilizing agents. Furthermore, GLD is known to be useful as an intermediate in the synthesis of glycidyl ethers, esters, amines, as well as glycidyl carbamate resins and polyurethanes. It has therefore found application in a variety of industrial fields including textile, plastic, pharmaceutical, cosmetic and photochemical industries.

Known commercial processes for the preparation of GLD include epoxidation of allyl alcohol using hydrogen peroxide and a tungsten-oxide based catalyst, and the reaction of epichlorohydrin with bases. However, there are drawbacks relating to these processes. For instance, the epoxidation of allyl alcohol involves several process steps and suffers problems relating to decomposition of the catalyst. Meanwhile, the high cost of raw materials and/or the management of waste by-products are a concern in both cases.

Glycerol (GLY) is produced in large quantities as a by-product in the production of biodiesels. With an increasing focus on the use of biofuels to at least partly replace petroleum fuels, the production of glycerol has increased to levels far higher than current demand. As a result, GLY is a cheap and readily available material, particularly in countries where production of biofuels is prevalent, and there has been an increased focus on the development of suitable applications of GLY.

The use of GLY in the preparation of glycerol carbonate (GLC), which may in turn undergo decarboxylation to form GLD, is well known. For example, GLD has historically been reacted with urea or transesterified with dialkylcarbonates/alkylene carbonates, as a means for producing GLC. Numerous methods are known for the subsequent conversion of GLC to GLD by decarboxylation.

U.S. Pat. No. 2,856,413 discloses decarboxylation of GLC to form GLD, where the conversion is catalysed by neutral metal salts, preferably those comprising either alkali or alkaline earth metals. The decarboxylation is performed under elevated temperature, preferably in the range of from 175° C. to 225° C., and at sub-atmospheric pressure.

U.S. Pat. No. 7,888,517 describes a method for improving the yield of GLD from decarboxylation of GLC by reducing a content of a salt having weak acidity (for example, sodium sulfate) in the crude GLC, for instance by distillation, neutralization or absorption, to 1500 ppm by mass or less before conducting decarboxylation, preferably in the presence of a catalyst.

US 2014/0135512 and US 2015/0239858 are also directed to the decarboxylation of GLC to form GLD and teach the use of an ionic liquid catalyst or an acid-base salt catalyst, respectively. These disclosures also advocate the use of a high-boiling point solvent, containing no active hydrogen (e.g. alcohol groups), for improving the selectivity of the conversion. Examples of high-boiling point solvents include polyethylene glycol dimethyl ether, dibenzyl ether and dibutyl phthalate. However, use of dibutyl phthalate or dioctyl phthalate can be complicated as a result of their toxicity and it has also been found by the present inventors that polymer formation can be an issue when these solvents are used. In addition, these solvents are also relatively expensive.

J. S. Choi et al., Journal of Catalysis, 297, 2013, pages 248 to 255 (hereinafter referred to as "Choi et al") reports the results of an investigation into the effect of temperature on conversion of GLC to GLD in the presence of ionic liquid catalyst. In order to maximise selectivity for GLD, Choi et al teaches to: i) use a high-boiling point solvent; ii) minimise the interaction of GLD with the ionic liquid catalyst; and iii) remove GLD product as soon as it is formed (the latter being achieved in Choi et al by performing the reaction at a reduced pressure).

U.S. Pat. No. 6,316,641 discloses the preparation of GLD from GLC employing a solid/liquid reaction system comprising a polyol solvent, such as glycerol or polyglycerol, and a solid catalyst consisting of type A zeolite or γ-alumina. The polyol solvent is said to act as both a carrier, preventing thermal decomposition of GLC, and a proton donor, facilitating opening and closing of the carbonate ring to form the epoxy ring once GLC is absorbed onto the catalyst surface. GLD is produced in the gaseous form following decarboxylation and diffuses away from the catalyst surface.

U.S. Pat. No. 7,868,192 discloses a process for the liquid-phase conversion of GLC to GLD by subjecting GLC to decarboxylation in the presence of a solvent containing no active hydrogen and preferably having a boiling point higher than GLD and preferably where the reaction is conducted in the presence of a Lewis acid catalyst. The decarboxylation reaction may be conducted in a thin film reactor, which facilitates separation of GLD as it is produced. Use of the solvent having no active hydrogen is said to improve selectivity for GLD by suppressing unwanted side reactions.

Historically, there have been conflicting reports in the patent literature regarding how to improve selectivity and yield of GLD from the decarboxylation of GLC. For instance, the above cited patent literature variously advocates different catalyst systems and/or different solvent conditions, either including a proton donor or conversely including no active hydrogen species. However, it has come to the attention of the present inventors that yields of GLD following GLC decarboxylation reported in the prior art may in fact be unreliable and may not accurately reflect the true achievable yields. In particular, it has been found that the method by which the crude reaction product is analysed can give a false impression of the level of decarboxylation that has occurred. Specifically, the process of performing gas chromatography (GC) analysis has been found to give rise to a level of decarboxylation of unreacted GLC which can then give a false impression of the true extent of decarboxylation in the reaction mixture.

The above impact of GC analysis on the determination of GLD yield has, most notably, led to a retraction of Green Chemistry article: Bai. R et al., "One-pot synthesis of glycidol from dimethyl carbonate over a highly efficient and easily available solid catalyst $NaAlO_2$", Rongxian Bai, et al., Green Chem., 2013, 15, pages 2929-2934. In the published retraction (Green Chem., 2016, 18, page 6144), it was reported that further investigation by $^1H$ NMR revealed that upon analysis of the product by GC, glycidol was formed due to decomposition of GLC at high temperature. On this basis, it was concluded that the NaAlO$_2$ catalyst was only effective at converting GLY to GLC, and not for converting GLC to GLD.

This realisation has therefore cast doubt on the effectiveness of GLC decarboxylations reported historically in the prior art and goes some way to explain why a significant number of such processes have not been taken up on a commercial scale. Thus, there remains a need for alternative processes for the conversion of GLC to GLD which maximise conversion and selectivity for GLD and which preferably also obviate the need for a decarboxylation catalyst.

The present invention is based on the surprising discovery that it is advantageous to react GLC in the liquid phase in the presence of a certain class of decarboxylation promotor, which may also serve as a solvent. The decarboxylation promotor fulfils multiple roles in the process of the present invention. In addition to promoting decarboxylation, the decarboxylation promotor serves as a solvent for the reaction as well an inhibitor of GLC self-polymerisation. The use of the decarboxylation promotor therefore contributes substantially towards the conversion of GLC and selectivity towards GLD. In addition, the use of an evaporator, such as an agitated thin-film evaporator, has been found to be particularly well suited for removing thermally unstable GLD from the reaction mixture as it is formed, so as to minimise unwanted GLD polymerisation and by-product formation, thereby further enhancing yield of GLD.

The process of the present invention, obviates the use of a decarboxylation catalyst commonly relied upon in prior art methods and also allows for a homogeneous reaction mixture to be used. This has advantages in terms of simplification of reaction apparatus, and maintenance thereof, and also means that the process of the present invention may be readily operated on a continuous basis.

Thus, in a first aspect, the present invention provides a process for the preparation of glycidol by thermal decarboxylation of glycerol carbonate, said process comprising the steps of:
a) contacting liquid glycerol carbonate with a decarboxylation promotor, having a boiling point of at least 160° C. at atmospheric pressure and consisting essentially of an aliphatic mono-ol, an aliphatic polyol, or mixtures thereof, to form a liquid phase mixture;
b) applying heat to the liquid phase mixture formed in step a) to induce thermal decarboxylation of the glycerol carbonate; and
c) separating glycidol formed in step b) from the liquid phase mixture by evaporation of glycidol; and
wherein the process does not comprise the use of a decarboxylation catalyst.

In another aspect, the present invention provides the use of a mono-ol, a polyol, or mixtures thereof, as a decarboxylation promotor for increasing the selectivity of the reaction of glycerol carbonate for the formation of glycidol.

In a further aspect, the present invention provides the use of a mono-ol, a polyol, or mixtures thereof, as a polymerisation inhibitor in a thermal decarboxylation of glycerol carbonate to form glycidol.

It has been surprisingly found that high conversion and selectivity for the formation of GLD may be obtained, even in the absence of a decarboxylation catalyst, by thermally decarboxylating GLC in the presence of the decarboxylation promotor in a liquid phase reaction mixture where GLD formed is separated by evaporation. Eliminating the requirement for a decarboxylation catalyst, particularly where a solid catalyst is employed, is particularly beneficial in terms of simplifying reactor design, simplifying the isolation and purification of co-product polyglycerols, reducing capital costs associated with providing and maintaining catalyst beds, and also reducing maintenance and cleaning requirements of the process equipment.

Following substantial investigations by the inventors, it has been found that the presence of the decarboxylation promotor advantageously modifies the selectivity of the process towards decarboxylation. Specifically, it is believed that the promotor reacts with glycerol carbonate to form a precursor adduct which subsequently undergoes decarboxylation so as to form glycidol and carbon dioxide. Formation of the precursor adduct facilitates decarboxylation, where this would be less prevalent in the absence of the decarboxylation promotor following a unimolecular reaction of glycerol carbonate. Moreover, it has been found that the decarboxylation promotor also acts as a polymerisation inhibitor, by acting as a chain terminator preventing self-polymerisation of glycerol carbonate to form either polyglycerols or poly(glycerol carbonate).

The term "decarboxylation promotor" used herein is intended to refer to an agent, or agents, that increase selectivity of the reaction of GLC towards the formation of GLD by decarboxylation. More specifically, the decarboxylation promotor used in connection with the present invention consists essentially of a mono-ol, a polyol, or mixtures thereof, and has a boiling point of at least 160° C. at atmospheric pressure.

The term "decarboxylation catalyst" used herein is intended to refer to an agent, or agents, that is/are expressly used to lower the activation energy of the decarboxylation reaction of GLC. Typical examples of decarboxylation catalysts that are excluded from the process of the present invention include solid catalysts, such as aluminosilicates (e.g. zeolites), alumina and silica-alumina, and metal salts, such as alkali metal salts and alkaline earth metal salts.

The term "evaporator" used herein is intended to refer to any device which is adapted for the evaporation of liquids by heat exchange and capable of evaporating GLD from a reaction mixture comprising GLC and the decarboxylation promotor. Examples of suitable evaporators for use in connection with the present invention include falling film evaporators, rising film evaporators, rising-falling film evaporators, agitated thin-film evaporators, long-tube evaporators, short-tube evaporators, batch pan evaporators, multiple-effect evaporators, plate-type evaporators (including climbing and falling-film plate evaporators), vapour-compression evaporators and forced circulation evaporators.

Preferably, the types of evaporator used in connection with the present invention are rising film evaporators, falling film evaporators, agitated thin-film evaporators, and forced circulation evaporators; more preferably falling film evaporators, agitated thin-film evaporators and forced circulation evaporators; even more preferably falling film evaporators and agitated thin-film evaporators; and most preferably agitated thin-film evaporators. These types of evaporators are characterized by low residence times and the capability of providing relatively high heat transfer coefficients.

In accordance with the process of the present invention, glycidol is prepared by the thermal decarboxylation of glycerol carbonate, said process comprising the steps of:
a) contacting liquid glycerol carbonate with a decarboxylation promotor, having a boiling point of at least 160° C. at atmospheric pressure and consisting essentially of an aliphatic mono-ol, an aliphatic polyol, or mixtures thereof, to form a liquid phase mixture;
b) applying heat to the liquid phase mixture formed in step a) to induce thermal decarboxylation of the glycerol carbonate; and
c) separating glycidol formed in step b) from the liquid phase mixture by evaporation of glycidol; and
wherein the process does not comprise the use of a decarboxylation catalyst.

The decarboxylation promotor used in the process of the present invention consists essentially, or consists, of a mono-ol, a polyol, or mixtures thereof, and has a boiling point of at least 160° C. It has been surprisingly found that mono-ols and polyols as described herein, as well as combinations thereof, serve to increase selectivity of the reaction of GLC towards the formation of GLD. Furthermore, it has been found that the presence of the decarboxylation promotor not only acts to increase selectivity toward the decarboxylation of GLC, it also acts a GLC polymerisation inhibitor, such that the formation of unwanted polymeric by-products is substantially avoided. In particular, it is believed that the decarboxylation promotor acts as a chain terminator preventing the formation of high molecular weight polymers that can give rise to undesirable solids formation, as discussed in more detail below.

Under typical thermal decarboxylation conditions, it has been found by the inventors that there is a problem of GLC self-polymerisation producing either poly(glycerol carbonate) solids (kinetic product) or polyglycerols (thermodynamic product), as illustrated in Scheme 1 below.

Scheme 1

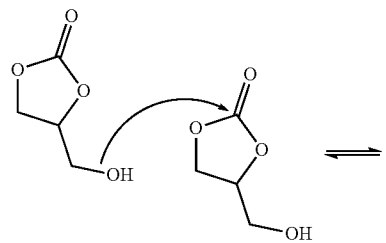

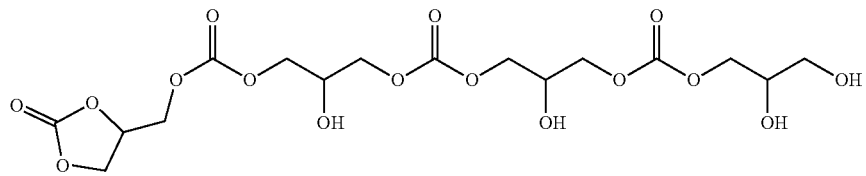

Poly(glycerol carbonate) solid

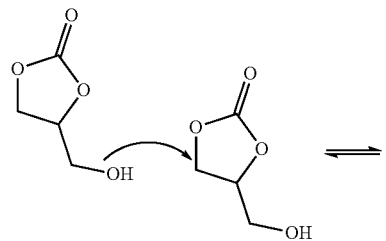

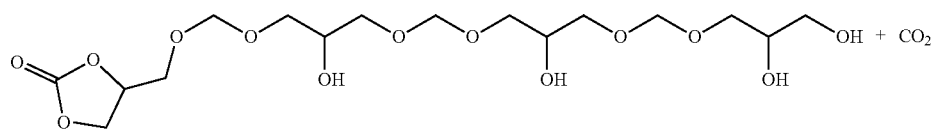

Polyglycerols

In contrast, in the presence of the decarboxylation promotor, it is believed that the GLC primarily undergoes nucleophilic addition from the decarboxylation promotor, thereby breaking the ring and forming a precursor adduct, as shown in Scheme 2, which does not readily take part in further bimolecular reactions under the reaction conditions of the process. Instead, the precursor adduct favours internal elimination and decarboxylation to afford GLD and $CO_2$, which is entropically favoured, as also shown in Scheme 2.

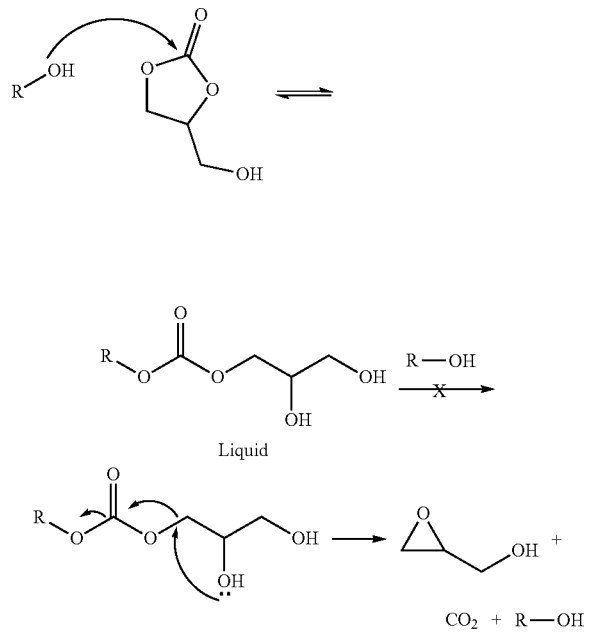

Scheme 2

To further investigate the impact of the decarboxylation promotor in the process of the present invention, additional experiments were conducted in the alternative preparation of propylene oxide from propylene carbonate, as shown below in Scheme 3.

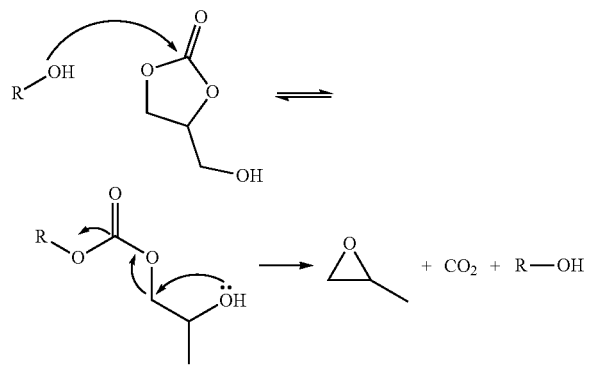

Scheme 3

As will be appreciated, in the thermal decarboxylation of propylene carbonate, no alcohol functionality is present in the molecule, prohibiting a unimolecular decarboxylation route, in contrast to glycerol carbonate. The inventors found that even with heating under reflux for prolonged periods, no thermal decarboxylation of propylene carbonate was found to occur. In contrast, in the presence of a decarboxylation promotor in the form of a mono-ol or a polyol as employed in accordance with the present invention, thermal decarboxylation of propylene carbonate occurred readily and with good yield of propylene oxide, the decarboxylation product. This suggests that unimolecular thermal decarboxylation in cyclic carbonates such as glycerol carbonate does not occur readily and also highlights that the decarboxylation promotor is effective at promoting the decarboxylation reaction.

Formation of glycidol in accordance with the present invention is therefore believed to occur via an adduct of the polyol and/or mono-ol with glycerol carbonate, and preferably principally via the adduct, as illustrated in Scheme 2. This would not be expected to be the case in conventional catalytic glycerol carbonate decarboxylations, even where polyol and/or mono-ol might be present incidentally as solvents. This is because the catalyst would be expected to compete such that decarboxylation proceeds via one or more alternative catalytic routes.

The decarboxylation promotor used in accordance with the present invention has a boiling point of at least 160° C. under atmospheric pressure. This ensures that the decarboxylation promotor can take part in the decarboxylation reaction without decomposing or readily evaporating from the liquid phase reaction mixture as a result of the elevated temperatures of the reaction. Preferably, the decarboxylation promotor has a boiling point of at least 180° C., more preferably of at least 200° C., at atmospheric pressure. In particularly preferred embodiments, the boiling point of the decarboxylation promotor, is from 220 to 250° C.

In some embodiments, the decarboxylation promotor is, or includes, a mono-ol. Reference to a "mono-ol" herein is intended to refer to an aliphatic hydrocarbyl group containing a saturated or unsaturated, linear or branched, hydrocarbyl chain comprising a single hydroxyl group (—OH) substituent and a major proportion of hydrogen and carbon atoms, and preferably consisting of only hydrogen, carbon and oxygen atoms. The mono-ol may include one or more saturated or partially unsaturated rings (e.g. cycloalkyl and cycloalkenyl groups). The carbon atom to which the hydroxyl group (—OH) is bonded is sp3 hybridized and the hydroxyl group (—OH) may be a primary, secondary or tertiary alcohol, preferably a primary alcohol. Preferably, the hydroxyl group (—OH) is not attached to a carbon atom of a ring. The mono-ol is not selected from glycerol carbonate or glycidol which, as will be appreciated, are the reactant and product of the decarboxylation. Examples of mono-ols include groups containing from 2 to 40 carbon atoms, such as from 10 to 30 carbon atoms or from 12 to 24 carbon atoms. Preferably, the mono-ol is a linear and/or saturated hydrocarbyl chain with a single hydroxyl group (—OH) substituent.

In preferred embodiments, one or more of the carbon atoms of a hydrocarbyl chain or ring of the mono-ol, and any substituents attached thereto, is replaced with an oxygen atom (—O—) which attaches to two carbon atoms (and not another oxygen atom linker) in the chain. In other words, the mono-ol may comprise one or more ether groups. For example, one or more methylene groups (—CH$_2$—) of a hydrocarbyl chain may each be replaced with an oxygen atom linker (—O—). Where one or more of the carbon atoms, and any substituents attached thereto, of the mono-ol is replaced with an oxygen atom (—O—), in preferred examples less than 50% of the carbon atoms, and any substituents attached thereto, are replaced with —O—, for example from 10 to 40% or from 15 to 30% of the carbon atoms are replaced.

In some embodiments, the mono-ol comprises one or more ether groups and is selected from monoethers, preferably monomethyl or monoethyl ethers, of polyethylene glycol and polypropylene glycol or monoethers, preferably monomethyl or monoethyl ethers, of oligomers of ethylene glycol and propylene glycol. Specific examples of mono-ols which comprise one or more ether groups include triethleneglycol monomethylether, triethleneglycol monoethylether, tripropyleneglycol monomethylether, tripropyleneglycol monoethylether and tetraethyleneglycol monomethylether.

In other embodiments, none of the carbon atoms of the mono-ol is replaced with —O— (i.e. the mono-ol does not include any ether groups).

Examples of mono-ols having a boiling point of at least 160° C. under atmospheric pressure and which do not include one or more ether groups (i.e. where none of the carbon atoms, and the substituents attached thereto, of the mono-ol are replaced) include fatty alcohols, which are preferably linear chain and/or saturated and which typically include the hydroxyl group at a terminal position of the molecule. Reference to a "fatty alcohol" used herein is intended to refer to a linear-chained, saturated or unsaturated, alcohol that is at least derivable, preferably derived, from natural fats and oils.

Fatty alcohols that may be used in the process of the present invention include those selected from $C_8$-$C_{40}$, preferably $C_{10}$-$C_{30}$, more preferably $C_{12}$-$C_{24}$ fatty alcohols. Specific examples of fatty alcohols include 1-nonanol, 1-decanol, 1-dodecanol, 1-hexadecanol, 1-octadecanol, and 1-nonadecanol. In embodiments, where a fatty alcohol is employed as the decarboxylation promotor, a solvent/co-solvent or alternatively another decarboxylation promotor may be used to improve the miscibility of the fatty alcohol with the GLC in the liquid phase mixture, if desired. For example, polyethylene glycol decarboxylation promotor may be used to improve the miscibility of the fatty alcohol. Alternatively, an inert solvent such as polyethylene glycol dimethyl ether or dibenzyl ether may be used instead.

Reference to a "polyol" herein is intended to refer to an aliphatic hydrocarbyl group comprising a plurality of hydroxyl groups (—OH) and a major proportion of hydrogen and carbon atoms, and preferably consisting of only hydrogen, carbon and oxygen atoms. The polyol may contain saturated or unsaturated, linear or branched, hydrocarbyl chains and/or one or more saturated or partially unsaturated rings. Each of the carbon atoms to which each of the plurality of hydroxyl groups (—OH) is bonded is sp3 hybridized and the plurality of hydroxyl groups (—OH) may independently be primary, secondary or tertiary alcohols. Preferably, the polyol comprises at least one primary alcohol. Examples of polyols include groups containing from 2 to 40 carbon atoms, from 2 to 30 carbon atoms, from 2 to 20 carbon atoms, from 2 to 10, or from 2 to 5 carbon atoms. In some embodiments, the polyol includes more than 2 hydroxyl groups, for example 3 to 10, 3 to 8, or 3 to 6 hydroxyl groups. In some embodiments, the polyol is a linear and/or saturated hydrocarbyl chain with a plurality of hydroxyl group (—OH) substituents.

In preferred embodiments, one or more of the carbon atoms of a hydrocarbyl chain or a ring of the polyol, and any substituents attached thereto, is replaced with an oxygen atom (—O—) which attaches to two carbon atoms (and not another oxygen atom linker) in the chain. In other words, the polyol may comprise one or more ether groups. For example, one or more methylene groups (—$CH_2$—) of the hydrocarbyl chain may each be replaced with an oxygen atom linker (—O—). Where one or more of the carbon atoms, and any substituents attached thereto, is replaced with an oxygen atom (—O—), in preferred examples less than 50% of the carbon atoms, and any substituents attached thereto, are replaced with —O—, for example from 10 to 40% or from 15 to 30% of the carbon atoms are replaced.

In some embodiments, the polyol comprises one or more ether groups and is selected from polyethylene glycol, polypropylene glycol, and oligomers of ethylene glycol, propylene glycol and glycerol. The molecular weight of polyethylene glycol and polypropylene glycol used in accordance with the present invention is preferably from 200 to 1000 Daltons, preferably from 200 to 750 Daltons, more preferably from 250 to 500 Daltons, most preferably from 200 to 400 Daltons.

Preferred oligomers of ethylene glycol, propylene glycol and glycerol include those having from 2 to 5 repeat monomer units. Specific examples of such oligomers include tripropylene glycol, tetrapropylene glycol, triethylene glycol, tetraethylene glycol, diglycerol, triglycerol, and tetraglycerol.

In some embodiments, the polyol is an oligomer of glycerol, preferably wherein the oligomer of glycerol is formed from 2 to 8 repeat monomer units, more preferably from 2 to 5 repeat monomer units, most preferably 2 or 3 monomer units.

In other embodiments, the polyol incorporates an ether group within a ring so as to form a cyclic ether group. Particular examples of such polyols include sugars, for example, fructose, galactose, glucose, mannose, sucrose and xylose.

In other embodiments, none of the carbon atoms of the hydrocarbyl chain of the polyol is replaced with —O— (i.e. the polyol does not include any ether groups).

In some embodiments, the polyol is a vicinal polyol, preferably a $C_2$-$C_{20}$ vicinal polyol, more preferably a $C_2$-$C_{10}$ vicinal polyol, most preferably a $C_2$-$C_5$ vicinal polyol. Reference herein to a "vicinal polyol" is intended to mean a polyol with at least two hydroxyl groups in a vicinal relationship with each other, that is, they are attached to adjacent carbon atoms in the molecule, and includes sugars mentioned above. In some embodiments, the vicinal polyol is selected from sugar alcohols. Sugar alcohols include, but are not limited to, glycerol, arabitol, sorbitol, erythritol, xylitol, mannitol, lactitol and maltitol. Specific examples of preferred vicinal polyols that may be used in accordance with the invention include ethylene glycol, propylene glycol, glycerol, 1,2-butanediol, 2,3-butanediol and erythritol. Preferred vicinal polyols are selected from glycerol and erythritol, most preferably the vicinal polyol is glycerol.

In some embodiments, the decarboxylation promotor is a mixture of one or more mono-ols and one or more polyols, preferably wherein the one or more mono-ols are selected from monoethers, preferably monomethyl or monoethyl ethers, of polyethylene glycol and polypropylene glycol or monoethers, preferably monomethyl or monoethyl ethers, of oligomers of ethylene glycol and propylene glycol and the one or more polyols are selected from glycerol or an oligomer of glycerol.

In another aspect, the present invention also provides a process for the preparation of glycidol by thermal decarboxylation of glycerol carbonate, said process comprising the steps of:
  a) contacting liquid glycerol carbonate with a decarboxylation promotor, having a boiling point of at least 160° C. at atmospheric pressure and consisting essentially of a mono-ol, optionally in combination with an aliphatic polyol, to form a liquid phase mixture, wherein the mono-ol is a phenyl substituted $C_1$ to $C_6$, linear or branched chain, alkylhydroxy group;

b) applying heat to the liquid phase mixture formed in step a) to induce thermal decarboxylation of the glycerol carbonate; and c) separating glycidol formed in step b) from the liquid phase mixture by evaporation of glycidol; and wherein the process does not comprise the use of a decarboxylation catalyst.

In the above further aspect, reference to a "phenyl substituted $C_1$ to $C_6$, linear or branched chain, alkylhydroxy group" is intended to refer to a $C_1$ to $C_6$ alkyl chain substituted by: i) a single hydroxyl (—OH) group; and ii) a phenyl group. The hydroxyl group may be primary, secondary or tertiary, preferably primary.

In a preferred embodiment of this further aspect of the invention, the mono-ol is benzyl alcohol.

In the above aspects of the invention, contacting of the liquid GLC with the decarboxylation promotor in step a) may be performed in any conventional manner depending on the container and means for applying heat to the liquid phase mixture in step b) and/or achieving evaporation in step c) of the process. The liquid GLC and decarboxylation promotor may, for instance, be added separately and mixed within a container (e.g. a chamber within a reactor) to which heat is to be applied. Alternatively, the liquid GLC may be preferably pre-mixed with the decarboxylation promotor before being introduced to a container to which heat is to be applied.

The decarboxylation promotor may be mixed with the liquid GLC in any suitable ratio that affords a desired level of selectivity and conversion to GLD in the thermal decarboxylation reaction. Suitably, the liquid GLC may, for instance, be contacted with the decarboxylation promotor in step a) so as to form a liquid phase mixture where the decarboxylation promotor is present in an amount of from 5 to 300 mol. % based on the combination of glycerol carbonate and decarboxylation promotor. In preferred embodiments, the decarboxylation promotor is present in an amount of from 5 to 70 mol. %, more preferably wherein the decarboxylation promotor is present in amount of from 10 to 40 mol. %, even more preferably wherein the decarboxylation promotor is present in amount of from 15 to 35 mol. %, most preferably in amount of from 20 to 30 mol. %.

As will be appreciated, the composition of the liquid phase mixture will change over the course of the reaction. Where the process is operated on a continuous basis, the ratio of decarboxylation promotor and liquid GLC may be continuously monitored and the composition of the feed(s) supplying the reaction mixture may be modified to maintain a desired ratio of decarboxylation promotor and liquid GLC.

Evaporation in step c) of the process may be conducted by any suitable means provided that gaseous GLD may be separated from the liquid phase reaction mixture, and preferably in a manner compatible with a continuous process. Preferably, evaporation in step c) is conducted using the same apparatus as employed for applying heat to the liquid phase reaction mixture in step b). Application of heat to the liquid phase mixture and evaporation of GLD may conveniently be undertaken in a device specifically configured for evaporation of liquid streams, i.e. an evaporator, supplied with one or more feeds for introducing liquid GLC and the decarboxylation promotor.

In preferred embodiments, prior to evaporation step c), a turbulent film of the reaction mixture is formed. Formation of a turbulent film is a means for facilitating thorough mixing of the liquid GLC and the decarboxylation promotor and for facilitating evaporation of GLD which is formed. Formation of a turbulent film may therefore be used as a means for conserving thermal energy and for inducing evaporation of GLD in a thermally sensitive manner.

The term "turbulent film of the reaction mixture" used herein is intended to refer to a film of reaction mixture which exhibits turbulent, non-laminar flow. Turbulent flow is typically characterised by the presence of eddies, vortices and/or other flow instabilities. Laminar flow, in contrast, is characterized by smooth, constant fluid motion. When flow is turbulent, particles of a liquid exhibit additional transverse motion which enhances the rate of energy and momentum exchange between the particles, thereby increasing heat transfer. Turbulent flows are known to exhibit higher Reynolds numbers than laminar flows, the Reynolds number being defined as the ratio of inertial forces of a flowing fluid to the viscous forces of the fluid or the ratio of the convective transport to the molecular transport of momentum.

The gradual transition from laminar flow to turbulent flow generally occurs with the increase of Reynolds number from 1,000 to 4,000. Reynolds numbers of above 4,000 may be considered to correspond to turbulent flow whilst Reynolds numbers of less than 2,000 are considered to correspond to laminar flow. Reynolds numbers of greater than 2,000 and less than 4,000 are considered to be transitional flows. Preferably the Reynolds number of the turbulent film formed is greater than 5,000, more preferably greater than 7,500, even more preferably greater than 10,000.

A turbulent film of reaction mixture may be provided, for example, through the use of an agitated thin-film evaporator which is capable of providing Reynolds numbers of greater than 10,000. The flow pattern in an agitated thin-film evaporator may be considered to be a combination of rotational or tangential film flow induced by the mechanical agitation of the rotor assembly of the evaporator as well as a downward or axial flow. In this case, the Reynolds numbers may be further characterized as rotational Reynolds numbers ($Re_R$), which extend the concept of the Reynolds number criteria to a rotational/annular flow, as in the case of an agitated thin-film evaporator. Preferably the rotational Reynolds number ($Re_R$) of the turbulent film formed in an agitated thin-film evaporator is greater than 5,000, more preferably greater than 7,500, even more preferably greater than 10,000.

The flow pattern in an agitated thin-film evaporator may be analyzed, for instance, using ANSYS-CFX 10.0 software and the rotational Reynolds number may be determined as described in Pawar et al., "CFD analysis of flow pattern in the agitated thin film evaporator", Chemical Engineering Research and Design, 2012, Volume 90, Issue 6, Pages 757-765, the disclosure of which is incorporated herein by reference. Ranade, V.V., "Computational Flow Modeling for Chemical Reactor Engineering", Volume 5, 1st Edition, 2002, Academic Press, also provides information regarding Reynolds stress models and determination of Reynolds numbers in turbulent flow processes, the disclosure of which is also incorporated herein by reference.

The term "agitated thin-film evaporator" used herein is intended to refer to any form of evaporator which provides a turbulent liquid film using mechanical agitation and typically comprising heated body and rotor assemblies. The term "agitated thin-film evaporator" used herein is also intended to encompass "wiped film evaporators" and the like. Agitated thin-film evaporators are, for instance, described in W. L. Hyde and W. B. Glover, "Evaporation of Difficult Products", Chemical Processing, 1997, 60, 59-61, and W. B. Glover, "Selecting Evaporators for Process Applications", CEP magazine, December 2004, published by AIChE. Agitated thin-film evaporators and assessment of flow patterns therein are also described in Pawar et al., "CFD analysis if flow pattern in the agitated thin film evaporator", Chemical Engineering Research and Design, 2012, Volume 90, Issue 6, Pages 757-765.

Agitated thin-film evaporators are widely used for the separation of volatile compounds from less volatile ones using efficient heat transfer and mechanical agitation to prevent decomposition of thermally sensitive liquids. In particular, these evaporator types are extensively used in the distillation of high boiling and temperature sensitive organics. Advantages of agitated thin-film evaporators include: i) short residence time for feed and low thermal stress; ii) high turbulence of liquid films; iii) narrow residence time distribution for desired condensate; iv) rapid surface renewal of the film on the inner evaporator wall; and v) energy savings from more efficient heat transfer.

The agitated thin-film evaporator which may be used in accordance with the present invention may be vertical or horizontal, preferably vertical. The rotor assembly of the agitated thin-film evaporator may include blades, examples of which include zero-clearance type (commonly referred to as "wiped-film" or "hinged blade"), rigid fixed clearance type or, in the case of a tapered rotor, adjustable-clearance type blade configurations. Alternatively, the agitated thin-film evaporator may have a rotor assembly comprising wipers, examples of which include roller wipers or spring-loaded block wipers. Where wipers are used, roller wipers are generally preferred for their ability to provide a consistent wiped film thickness distributed over the evaporator inner wall, to provide a homogeneous material layer across the evaporator with mixing action, to promote high evaporation rates; and obviate bottom seals thereby minimizing the potential for vacuum leaks. Agitated thin-film evaporators are available from suppliers such as LCI Corporation (North Carolina, US), Pfaudler (US), UIC GmbH (Germany) and Pope Scientific Inc (Wisconsin, US).

When an agitated thin-film evaporator is used, a mixture of liquid GLC and decarboxylation promotor is typically fed to an inlet of the evaporator from where the mixture is evenly distributed on the inner wall of the evaporator by the rotating blades or wipers, after which turbulent flow is developed in the liquid film, allowing optimum heat flux through the liquid and mass transfer to the vapour phase. In particular, movement of the wipers/blades is known to generate a fillet of liquid/bow wave in the liquid film, thereby creating turbulent flow. A fillet/bow wave may be formed, for example, as the volumetric flow rate of the liquid is increased so that the thickness of the film on the inner wall of the evaporator exceeds the thickness of a clearance between the wipers/blades and the inner wall. Roller wipers or spring-loaded block wipers do not, however, always maintain a clearance with the inner wall and therefore turbulent flow in these cases may be generated differently.

The skilled person is able to select a suitable volumetric flow rate in order to provide a thickness of film which exceeds the clearance between the wipers/blades and the inner wall in order to ensure turbulence in the liquid in the agitated thin-film evaporator. In addition, increasing rotor speed of the agitated thin-film evaporator generally increases the shear strain rate and therefore the Reynolds rotational number. Therefore, turbulence in the film may also be modified as desired by adjusting the rotor speed in the agitated thin-film evaporator.

In other embodiments, a falling film evaporator is used for the reaction and to separate GLD formed from the reaction mixture. Falling film evaporators generally comprise vertical or horizontal tubes and are characterized in that fluid to be evaporated flows downwards by gravity as a continuous film along the walls of the tubes from a fluid distributor. For low mass flows, the film flow in a fallingfilm evaporator can be laminar, whilst higher mass flows can mean that turbulent film flow is developed. A particular benefit of the falling film evaporator is that it is characterized by low residence time of the liquid and no requirement for superheating. Such evaporator types may also be used to evaporate GLD at temperatures much lower than its boiling point. Falling film evaporators are available from suppliers such as Sulzer (Switzerland) and GEA (Germany).

In other embodiments, a rising film evaporator is used for the reaction and to separate GLD formed from the reaction mixture. Rising film evaporators, like falling film evaporators, are a form of shell and tube heat exchanger. The liquid being evaporated is generally fed from the bottom into long tubes and heated with heating medium condensing on the outside of the tube from the shell side. The design of long vertical tubes in rising film evaporators promote the formation of a long, thin and continual film of liquid formed by the pressure exerted by the vapour which occupies the centre part of the tube and rises up. This ascending motion of film and vapour in the centre promotes the formation of a turbulent film. Such evaporator types may also be used to evaporate GLD at temperatures much lower than its boiling point. Falling film evaporators are available from suppliers such as Rufouz Hitek Engineers Pvt. Ltd. (India).

In other embodiments, a forced circulation evaporator is used for the reaction and to separate GLD formed from the reaction mixture. Forced circulation evaporators are characterised by the use of both heat exchangers and flash separation units in conjunction with circulation of the liquid by means of a circulation pump. The liquid is constantly circulated through the system. The circulating liquid is generally superheated under pressure upon a short contact time with the heat exchanger before the liquid enters a flash vessel where pressure is reduced to induce flash evaporation. Forced circulation evaporators are available from suppliers such as GEA (Germany).

Generally, where an evaporator is used, liquid GLC and the decarboxylation promotor are preferably combined prior to being fed to the evaporator. In some embodiments, the evaporator is supplied with a feed used to provide, or supplement, the content of decarboxylation promotor in the liquid mixture in the evaporator. However, it is preferred that the provision of any supplemental decarboxylation promotor, such as that obtained from any recycling steps, be pre-mixed with a GLC-containing feed stream which is subsequently fed to the evaporator.

Liquid GLC and the decarboxylation promotor are preferably supplied to the evaporator at a controlled rate. The rate at which liquid GLC and decarboxylation promotor may be fed to the evaporator is not particularly limited. However, by controlling the rate at which GLC is fed to the evaporator, it is possible to optimise the evaporation rate of GLD formed inside the evaporator, as well as the thickness of any liquid film of reaction mixture that may be formed in some evaporators discussed hereinbefore and the extent of the turbulence formed therein. The feed flow rate may of course fluctuate or be modified during the course of the process, for instance in response to the prevailing rate of GLD formation and separation, and still correspond to a controlled flow.

Generally, it is preferred that the liquid GLC is introduced into the evaporator at a rate which is greater than or equal to the rate of evaporation of GLD formed in the evaporator. For an agitated thin film evaporator, this helps avoid the situation where the thickness of the liquid film on the inner wall of the evaporator is reduced to an extent that turbulent flow is lessened, thereby making heat transfer and evaporation less efficient. For falling and rising film evaporators, higher flow rates lead to increased turbulence in the films generated therein meaning higher heat transfer coefficients are obtainable.

Controlling the rate at which liquid GLC is fed into the evaporator also helps to avoid the evaporator from drying out, for example such that a liquid film is not continuous or properly maintained on an inner wall in the case of rising/falling film evaporators or agitated thin-film evaporators. Drying out of the liquid film on the inner wall of these evaporators not only prevents the formation of turbulent flow of liquid but also exacerbates the formation of by-products, such as solid hyperbranched polyether polyols (as shown in FIG. 1a), which may take the form of solid deposits in the evaporator. Where, for instance, the boiling point of the decarboxylation promotor is lower than GLC, drying out of the evaporator may be a consequence of a majority of the decarboxylation promotor having evaporated without being adequately replenished. Remaining unreacted GLC may then undergo self-polymerisation forming polyols which cannot be terminated in the usual manner by virtue of the presence of the decarboxylation promotor as discussed hereinbefore. This therefore results in solids build-up. An absence of any flowing condensate liquid exiting out of the bottom of the evaporator also prevents any solids from being carried out of the evaporator, as may otherwise occur, further exacerbating solid build-up inside the evaporator. Thus, ensuring a constant liquid film on the inner wall of these evaporators reduces unwanted by-products and reduces the cleaning and maintenance requirements.

The flow rate, in terms of feed mass/(surface area of reactor * time), at which the liquid feed stream comprising GLC is fed to the evaporator may suitably be in the range of from 0.001 to 0.250 $kgm^{-2}s^{-1}$. In some embodiments, the flow rate is from 0.005 to 0.050 $kgm^{-2}s^{-1}$, preferably from 0.008 to 0.015 $kgm^{-2}s^{-1}$.

Any suitable means for feeding the liquid GLC and decarboxylation promotor to the evaporator may be used in accordance with the present invention. Preferably a pumping means is provided in order to pump the liquid phase mixture for feeding to the evaporator in a controlled manner and at a particular flow rate, although preferably one which is configured for use in connection with systems operating under vacuum and also preferably flow meter controlled. In that regard, the combination of gear pump and backpressure regulator/overflow valve have been found to be particularly suitable for this purpose. An example of a suitable flowmeter controlled gear pump is the Bronkhorst® gear pump with integrated Coriolis mini-CORI-FLOW™ mass flow meter available from Bronkhorst UK.

As mentioned above, rotor speed in an agitated thin-film evaporator can have a significant effect on shear strain rate and the level of turbulence provided to the liquid film therein. Thus, where an agitated thin-film evaporator is employed in connection with the present invention, the rotor speed in the agitated thin-film evaporator is suitably greater than 25 rpm in order to ensure turbulent flow is provided by the fillet/bow wave created in the film by the wipers/blades. In preferred embodiments, the rotor speed in the agitated thin-film evaporator is at least 50 rpm, more preferably at least 100 rpm, even more preferably at least 200 rpm and still more preferably at least 400 rpm. In other preferred embodiments, the rotor speed is less than 1500 rpm, more preferably less than 1250 rpm, even more preferably less than 1000 rpm. In particularly preferred embodiments, the rotor speed in the agitated thin-film evaporator is from 100 rpm to 1000 rpm, more preferably from 150 to 800 rpm, even more preferably from 200 to 600 rpm, most preferably from 250 rpm to 500 rpm.

The process of the present invention may be operated at sub-atmospheric pressure or may be operated at atmospheric or elevated pressures together with a flow of an inert carrier gas (for example, nitrogen) for facilitating evaporation and driving off GLD vapours, for instance as an effluent stream from an agitated thin-film evaporator. Therefore, in step b) of the process, the gaseous GLD formed may flow out of the evaporator under the action of a vacuum or by virtue of a flow of inert gas.

In preferred embodiments, the process is operated at sub-atmospheric pressure. Where an evaporator is employed, lowering the pressure at which the evaporator is operated lowers the temperature at which a particular rate of evaporation may be achievable and can also help reduce residence time and lessen by-product formation. For instance, the process of the invention, or an evaporator employed in the process, is suitably operated at pressures up to 50.0 kPa absolute (500 mbar absolute), for instance from 0.1 kPa absolute (10 mbar absolute) to 50.0 kPa absolute (500 mbar absolute). Preferably, the process of the invention, or an evaporator employed in the process, is operated at a pressure of less than or equal to 20.0 kPa absolute (200 mbar absolute), preferably less than or equal to 15.0 kPa absolute (150 mbar absolute), more preferably less than or equal to 12.5 kPa absolute (125 mbar absolute) and most preferably less than or equal to 11.0 kPa absolute (110 mbar absolute). A particularly preferred range of pressure is from 0.5 kPa absolute (50 mbar absolute) to 20.0 kPa absolute (200 mbar absolute The skilled person is able to select a suitable temperature range at which the process is operated based, for instance, on the desired evaporation rate of GLD and the volumetric flow of GLD-containing stream, for instance as an effluent from an evaporator. For example, where an agitated thin-film evaporator is employed, the skilled person is able to select the evaporator temperature depending on, for instance, the liquid GLC flow rate, rotor speed of the wipers/blades, the pressure under which the evaporator is operated and also based on whether the liquid GLC feed is preheated or not. Generally, suitable temperature ranges will preferably lead to a rate of evaporation that: i) avoids the liquid film being evaporated to dryness based on the flow rate; ii) minimises unwanted by-product formation; and iii) provides a desirable volumetric flow of gaseous GLD effluent from the evaporator.

Suitable temperature and pressure ranges may also be selected to minimise any unwanted evaporation of unreacted GLC and/or decarboxylation promotor from the liquid phase reaction mixture together with the GLD. By minimising such stripping of unreacted GLC and/or decarboxylation promotor, purification of the crude GLD product stream is less onerous or possibly even unnecessary.

Heating of the liquid GLC and decarboxylation promotor may be performed by any conventional means which is compatible with the means of evaporation employed (e.g. an evaporator). Examples include use of a circulating vapour or liquid heat transfer medium (for example, in a shell and tube heat exchanger configuration or in a jacketed heating system), use of band heaters or use of an inductive heating system employing wrap-around metal coils. Preferably, evaporation step c) of the process of the invention, or an evaporator employed in the process, is operated at a temperature of from 125° C. to 300° C., preferably from 190° C. to 275° C., more preferably from 200° C. to 250° C., even more preferably from 210° C. to 240° C., and most preferably from 215° C. to 235° C. For the avoidance of doubt, where an evaporator is employed, operation temperature of the evaporator is considered to correspond to the internal temperature of the evaporator, for instance as measured by thermocouple, and not, for example, the temperature of the inlet to the evaporator.

In some embodiments, where an evaporator is employed, the liquid GLC and decarboxylation promotor are preheated prior to being introduced into the evaporator. Preheating of the liquid GLC can reduce the viscosity of GLC, making it easier to pump, and may also lessen the degree of heating required with respect to the evaporator, which may be more energy efficient overall and may also improve evaporation rates. In some embodiments, the liquid GLC is preheated to a temperature of from 50° C. to 150° C., preferably from 65° C. to 135° C., more preferably from 75° C. to 125° C.

Where an evaporator is employed, the GLD vapours formed therein may be withdrawn from the evaporator, for example, counter-currently or co-currently to the liquid feed, through an outlet, usually toward or at the top of the evaporator in the case of a vertical evaporator. Typically, the evaporator also comprises an outlet for liquid condensate (also known as a "residue"), usually located toward or at the bottom of the evaporator. A collector vessel may be present which collects the liquid condensate/residue withdrawn from the evaporator which includes any unreacted GLC and decarboxylation promotor.

In preferred embodiments, unreacted GLC and/or decarboxylation promotor withdrawn from the evaporator as part of a liquid condensate/residue is recycled to the feed for the evaporator. For instance, a pumping means may be provided in order to transfer unreacted GLC and/or decarboxylation promotor from a collector vessel to the feed stream during the process. Thus, it is possible that liquid GLC may pass through the evaporator a number of times before being reacted to form GLD. Since conditions can be selected to minimise side reactions inside the evaporator, and the presence of the decarboxylation promotor itself has been found to be an effective inhibitor of GLC self-polymerisation, making multiple "passes" through the evaporator in this manner is not believed to be detrimental to selectivity but may significantly improve the overall level of GLC conversion. In some embodiments a gear pump is utilized, preferably a flow meter controlled gear pump, in order to recycle the unreacted GLC withdrawn from the evaporator back to the feed, preferably wherein recycling is operated on a continuous basis.

Following formation of GLD, a gaseous effluent stream from the evaporator comprising GLD vapours may be passed to a condenser for condensing condensable components of the gaseous effluent stream. Examples of suitable condensers include liquid-cooled surface condensers, which may be operated in transverse, parallel or counter flow. Non-condensables, for example carbon dioxide by-product, may be separated by using a gas-liquid separator downstream of the condenser.

$CO_2$ vapours produced by the decarboxylation reaction may be vented through the vacuum pump or fed to a $CO_2$ scrubber before being conveyed to downstream processes for capture and appropriate disposal. A cold condensation trap may also be utilised upstream of the vacuum pump so as to condense any remaining condensable vapours which may be detrimental to the vacuum pump.

A GLD liquid product stream may therefore be collected in a vessel. Optionally, the GLD product may undergo purification in order to remove unwanted by-products and/or any unreacted GLC or decarboxylation promotor that may have been stripped from the liquid phase reaction mixture together with the GLD. Preferably, final purification of the GLD obtained by the process of the invention is by thin film evaporation. As will be appreciated, any unreacted GLC and decarboxylation promotor obtained as result of the GLD purification may be recycled back to a feed stream to the evaporator, if desired. One by-product which may be produced as a result of a side reaction is glycerol (GLY). Scheme 4 below shows a possible reaction mechanism by which GLY may be produced.

Scheme 4

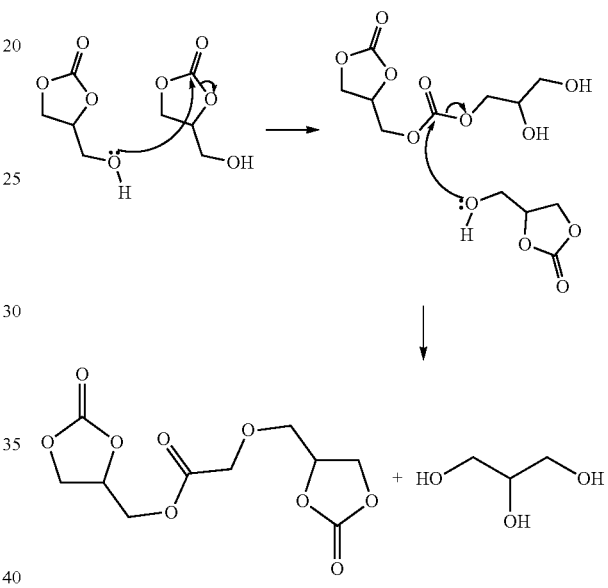

Another possibility is the reaction of GLD with any GLY that may be present so as to form diglycerol. GLD product may be isolated from GLY, diglycerol and unreacted GLC by separation using distillation or thin film evaporation. Any suitable reactive distillation column may be used provided that it has a number of stages (e.g. ideal stages) commensurate with the separation desired, for example fromt 1 to 10 ideal separation stages. As will be appreciated, one or more separation steps may also be employed to ensure adequate separation of GLD product from the crude material. Any of the agitated thin film evaporators discussed hereinbefore may be conveniently used for purification of the GLD product by thin film evaporation. Any glycerol that is isolated by means of the separation may be recycled to a GLC preparation process, such as the preferred GLC preparation process described hereinafter. Alternatively or additionally, if glycerol is employed as the decarboxylation promotor, or a component thereof, in the process, then the glycerol may be fed back to contacting step i) of the process, for instance a feed stream to an agitated thin-film evaporator employed in the process. Similarly, any unreacted GLC that is isolated following purification of the crude product of the process may be recycled back to contacting step i) of the process, for instance, as a feed stream for an agitated thin-film evaporator employed in the process.

Figure 1B:
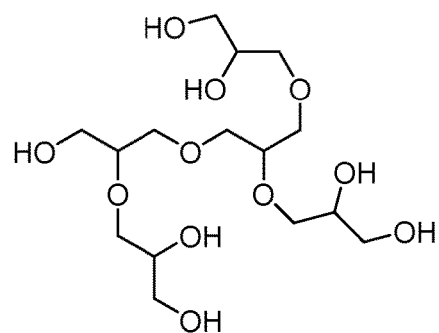

The process of the present invention has been found to afford only minor by-product formation and is capable of completely avoiding the production of high molecular weight by-products that are potentially damaging to process equipment. In addition to those discussed above, minor by-products of the present invention have been found to take the form of low molecular weight oligomers of glycerol, for instance, having from 2 to 5 repeat monomer units. An example of a low molecular weight oligomer of glycerol having 5 repeat monomer units is shown in FIG. 1b. As will be appreciated, this by-product may in fact be repurposed and used as the decarboxylation promotor in the reaction. Oligomers of glycerol are also useful as polymer additives (for example in polyesters), food additives (as polyglycerol esters), defoaming agents, as well as shale inhibitors in drilling fluids. Therefore, these by-products of the present invention can advantageously provide a further revenue stream in their own right and may be isolated from the crude product mixture by the separation techniques discussed herein.

Thus, in some embodiments, the process of the invention also comprises the formation of an oligomer of glycerol having from 2 to 8 monomer units, preferably from 2 to 5 monomer units, as a minor by-product. The yield of this by-product may be from 1 to 15 mol. %, preferably from 1 to 10 mol. %, more preferably from 1 to 5 mol. %. In some embodiments, this by-product is recycled to the decarboxylation reaction for use as a decarboxylation promotor. In alternative embodiments, this by-product is isolated from the crude product mixture for utilising as a commodity chemical.

As will be appreciated, the process of the present invention may be performed as a batch or preferably as a continuous process. Operating on a continuous basis is also facilitated based on there being no requirement for catalyst regeneration or solvent replacement.

The process of the present invention advantageously obviates the need for a decarboxylation catalyst that has typically been employed in prior art processes. This is particularly beneficial in terms of simplifying reactor design, simplifying the isolation and purification of product, reducing capital costs associated with providing and maintaining catalyst beds and also reducing maintenance and cleaning requirements of the process equipment. Therefore, so as to take full advantage of the benefits of the present invention, no decarboxylation catalyst is used to catalyse the decarboxylation reaction. Preferably, no solvents or other diluents, other than the decarboxylation promotor, are used which may be supplied with the GLC reactant. As the skilled person will appreciate, use of a solvent differs from the situation in which an inert gas is employed in connection with an evaporator, as in some configurations, discussed hereinbefore. Where a solvent is used in the present invention, the solvent is an inert solvent having no active hydrogens, for example, polyethylene glycol dimethyl ether or dibenzyl ether.

It has been found by the inventors that attempting to achieve decarboxylation and evaporation of GLD product in the absence of a catalyst inside an evaporator, such as an agitated thin-film evaporator, by conventional means gives a poor level of selectivity for GLD. In particular, the high temperatures required to promote thermal decarboxylation inside the evaporator were found to give rise to side reactions leading to the formation of unwanted by-products, particularly polymeric by-products such as solid hyper-branched polyether polyols, as shown in FIG. 1a. These by-products can take the form of solid deposits inside the evaporator, which can lead to poor performance and increased cleaning requirements of the evaporator, as well as in the form of contaminants in the liquid condensate/residue withdrawn from the evaporator.

In contrast, by including a decarboxylation promotor in accordance with the present invention, it has been found to be possible to prepare GLD in high yield and with high selectivity whilst avoiding the problems associated with non-catalytic methods. In particular, it has been found that the presence of the decarboxylation promotor not only acts to increase selectivity toward the decarboxylation of GLC, it also acts a GLC self-polymerisation inhibitor, by acting as a chain terminator thereby increasing selectivity toward for the formation of glycidol and thereby substantially reducing the formation of unwanted polymeric by-products, such as polyglycerols and poly(glycerol carbonate). By also separating GLD formed in the liquid phase by evaporation in a thermally sensitive manner, decomposition and/or by-product formation associated with the GLD product is also minimised, further enhancing the yield of GLD obtainable from the process.

In preferred embodiments, the yield of GLD in the process of the invention is at least 60 mol. %, more preferably at least 70 mol. %, most preferably at least 75 mol. %, as measured using NMR, for instance, $^1$H-NMR.

In other preferred embodiments, the level of GLC conversion is at least 90 mol. %, preferably at least 95 mol. %, more preferably at least 98 mol. %. In some embodiments where an evaporator is employed, this level of conversion is achieved through recycling of unreacted GLC obtained from the evaporator to the feed.

GLC employed in the process of the present invention may be prepared by known processes. In one example, GLC may be prepared from transesterification of GLY and dialkyl carbonate or cyclic alkylene carbonate, as illustrated below in Schemes A and B.

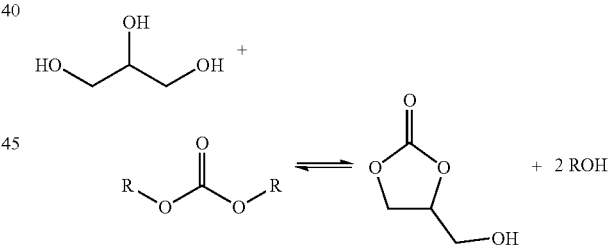

Scheme A

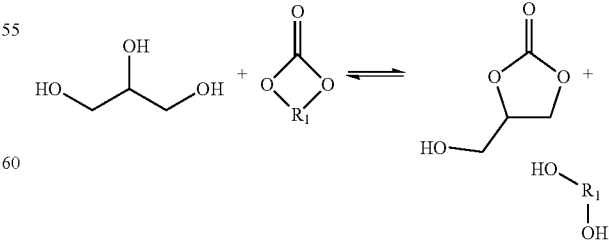

Scheme B

Purity of the GLC reactant stream is believed to be important for maximising GLC conversion and GLD selectivity. Therefore, it is preferred that a GLC reactant stream utilized in the present invention has the highest purity possible. For example, it is preferred that the purity of a GLC reactant stream used in the process of the present invention is at least 95%, more preferably at least 96%, even more preferably at least 97%, still more preferably at least 98% and most preferably the GLC reactant stream has a purity of at least 99%, as measured according to HPLC.

GLC for use in the present invention is readily available from suppliers such as Innospec Colorado, US) and UBE Industries Ltd (Japan). Typically methods for preparing GLC involve direct carbonylation of glycerol. Other common synthetic routes involve transesterification of dialkyl carbonates or cyclic alkylene carbonates with glycerol.

Preferably, the GLC used in the decarboxylation reaction of the present invention is prepared by a method comprising the steps of:
(i) contacting and partially reacting a glycerol reactant stream with: a) a dialkyl carbonate reactant stream, comprising greater than 80 wt. % dialkyl carbonate; and/or b) a cyclic alkylene carbonate reactant stream, comprising greater than 80 wt. % cyclic alkylene carbonate, in a first reaction zone in the presence of a homogeneous transesterification catalyst;
(ii) separating at least a portion of the alcohol by-product formed from the reaction of dialkyl carbonate and/or cyclic alkylene carbonate with glycerol in step (i) from the reaction mixture so as to obtain an alcohol-containing by-product stream;
(iii) reacting at least a portion of the remaining reactants in a second reaction zone in the presence of the homogeneous transesterification catalyst; and
(iv) obtaining a GLC product stream.

The process for preparing GLC according to the above method involves a transesterification reaction between GLY and dialkyl carbonate or cyclic alkylene carbonate, leading to the formation of GLC and alcohol by-product, as illustrated below in Schemes C and D.

Scheme C

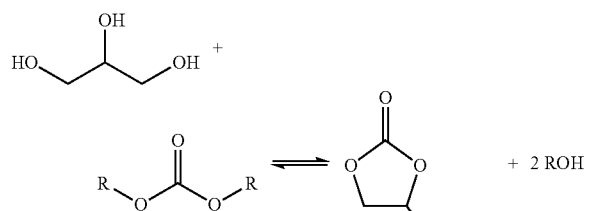

Scheme D

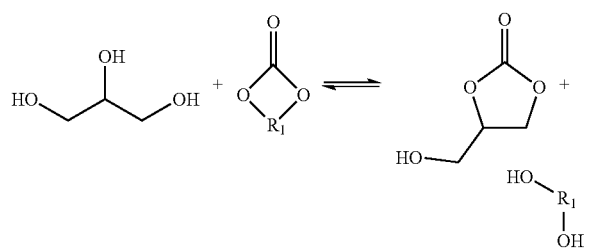

In preparing GLC for use in the process of the present invention, it has been found to be advantageous to initially allow the build-up of by-product alcohol following reaction of the reactant streams in step (i) and prior to an intermediate by-product alcohol removal step (ii). GLY and dialkyl carbonate streams are not normally miscible, resulting in a biphasic reaction mixture, which is believed to limit the rate of reaction of the reactants. However, it has been found that, following the production of by-product alcohol, the reaction mixture becomes monophasic, which is believed to be of benefit for the rate of reaction and the extent of GLY conversion. Furthermore, it has been surprisingly found that by incorporating an intermediate by-product alcohol separation step (ii) the conversion of GLY to GLC is enhanced. Overall conversion has also been found to be especially favoured when the by-product alcohol separation step (ii) involves distillation of the reaction mixture, as discussed hereinbelow.

Meanwhile, it has also been found that selectivity for GLC in the subsequent reaction in step (iii) of the above method which follows the alcohol separation step (ii) may be increased by ensuring that the subsequent reaction is performed with continuous by-product alcohol removal. It has been found that by incorporating continuous removal into the final stage of the reaction the overall selectivity for GLC increases. Without being bound by any particular theory, it is believed that formation of glycerol dicarbonate occurs more readily in the subsequent reaction in step (iii) following the methanol separation step (ii), as illustrated in Scheme E below.

Scheme E

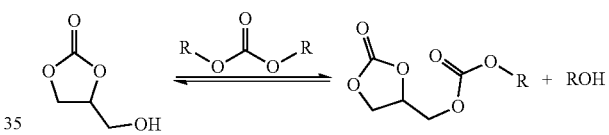

By employing continuous by-product alcohol removal in the final stage reaction in step (iii), it has been found that the equilibrium can be shifted towards the formation of the desired GLC, as illustrated in Scheme F below.

Scheme F

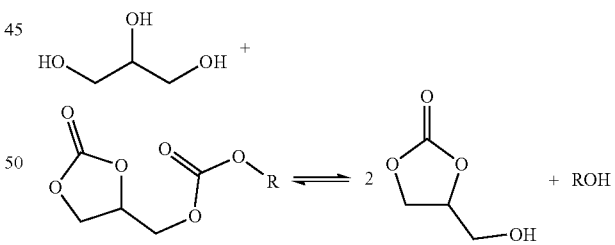

The combination of the intermediate by-product alcohol separation step (ii) followed by continuous by-product alcohol removal in the subsequent reaction step (iii) may therefore maximise both conversion as well as selectivity for GLC.

Further details of the above preferred method for preparing GLC for use in the present invention are found in WO 2017/125759, the content of which is incorporated herein by reference in its entirety.

The present invention also provides a process for the preparation of propylene oxide by the thermal decarboxylation of propylene carbonate, said process comprising the steps of:

a) contacting liquid propylene carbonate with a decarboxylation promotor, having a boiling point of at least 160° C. at atmospheric pressure and consisting essentially of an aliphatic mono-ol, an aliphatic polyol, or mixtures thereof, to form a liquid phase mixture;
b) applying heat to the liquid phase mixture formed in step a) to induce thermal decarboxylation of the glycerol carbonate; and
c) separating propylene oxide formed in step b) from the liquid phase mixture by evaporation of propylene oxide; and
wherein the process does not comprise the use of a decarboxylation catalyst.

As will be appreciated, all embodiments relating to other process aspects of the present invention including, for instance, the nature of the decarboxylation promotor and conditions of the decarboxylation reaction, apply equally to this further aspect of the invention.

Figure 2:
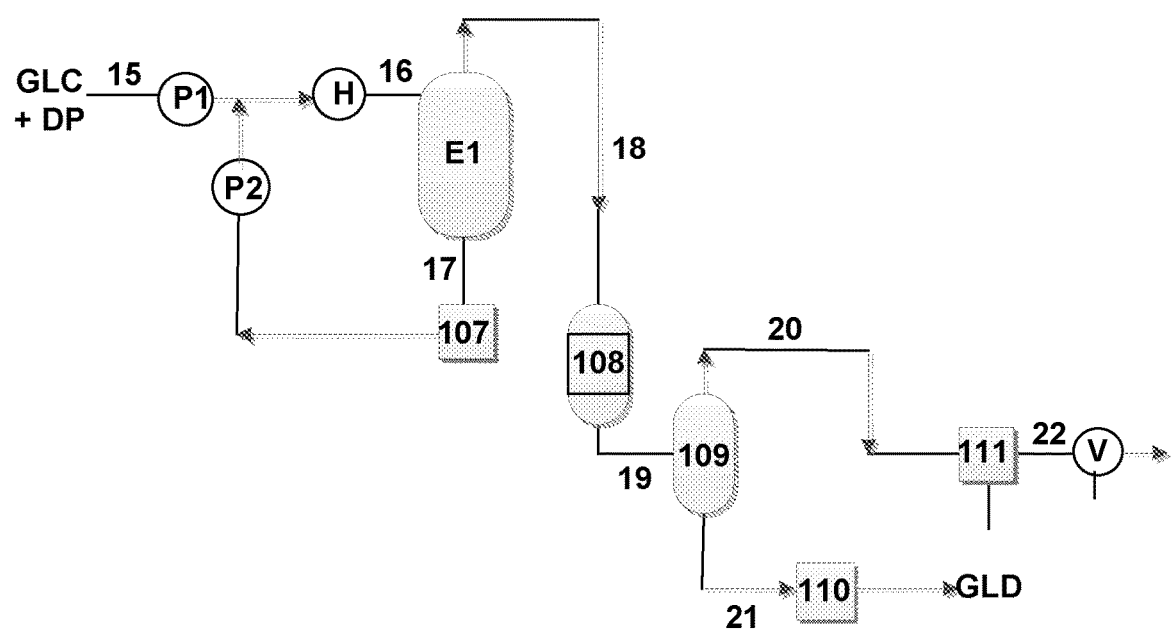
Figure 3:
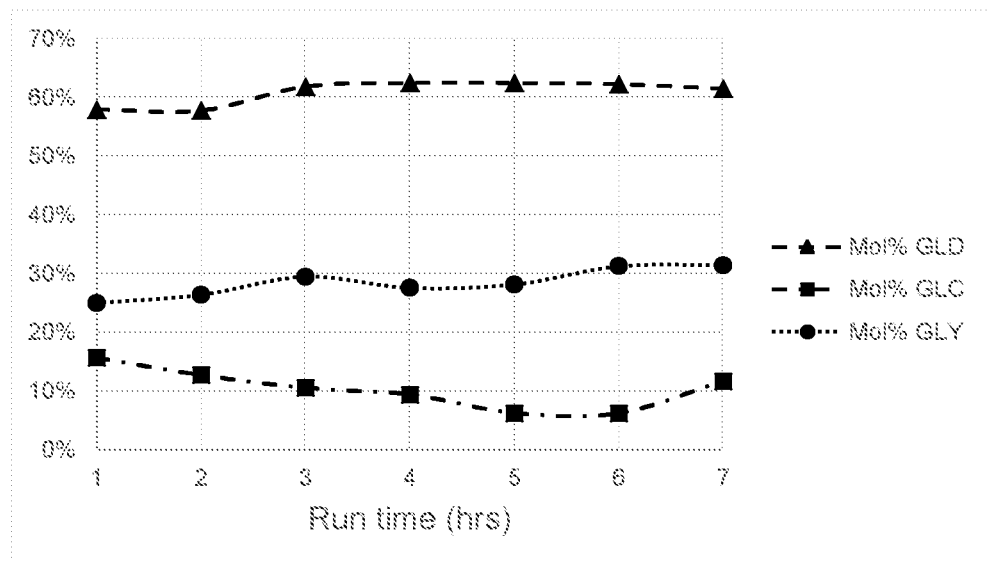
Figure 4:
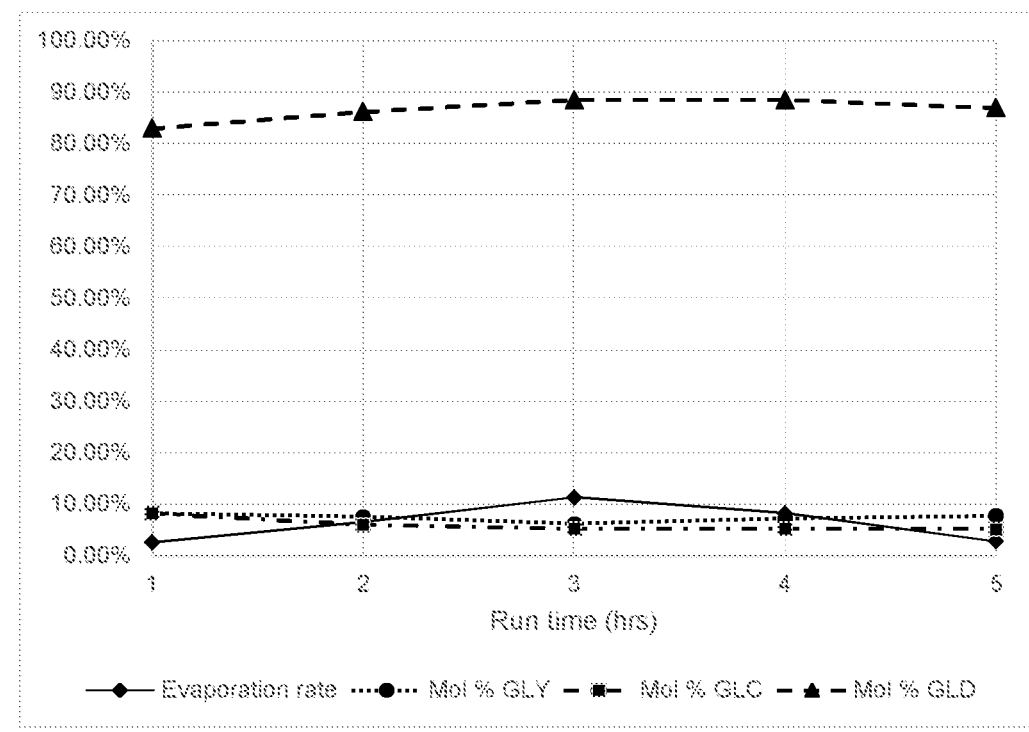
Figure 5:
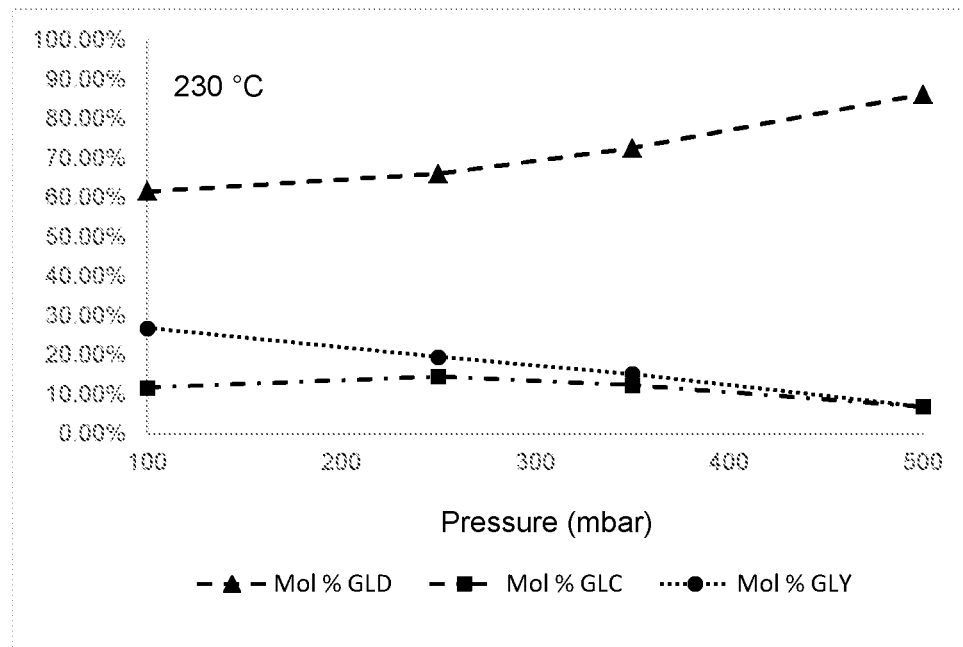
Figure 6:
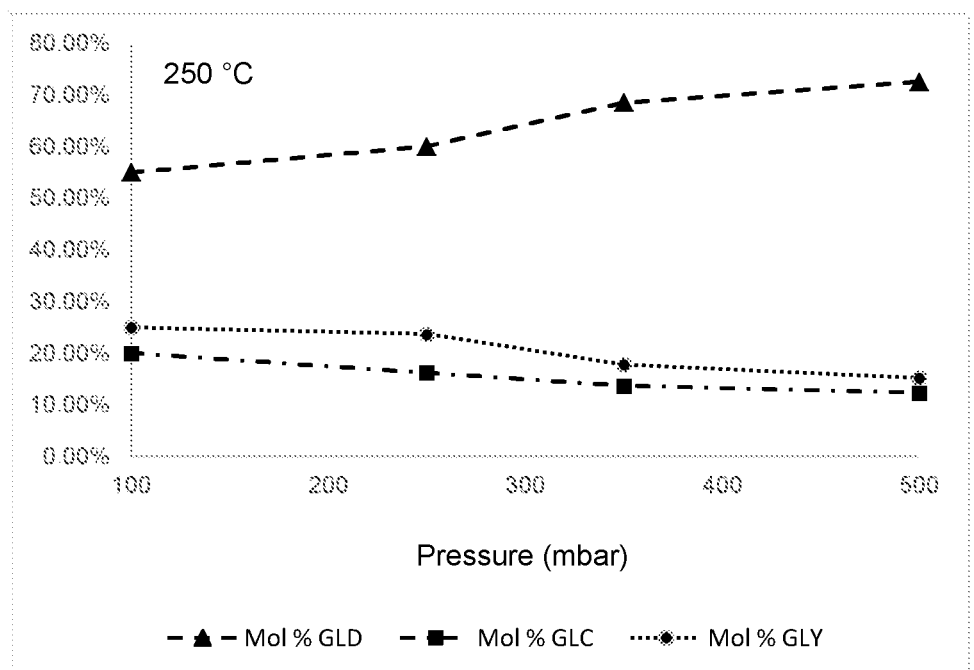
Figure 7:
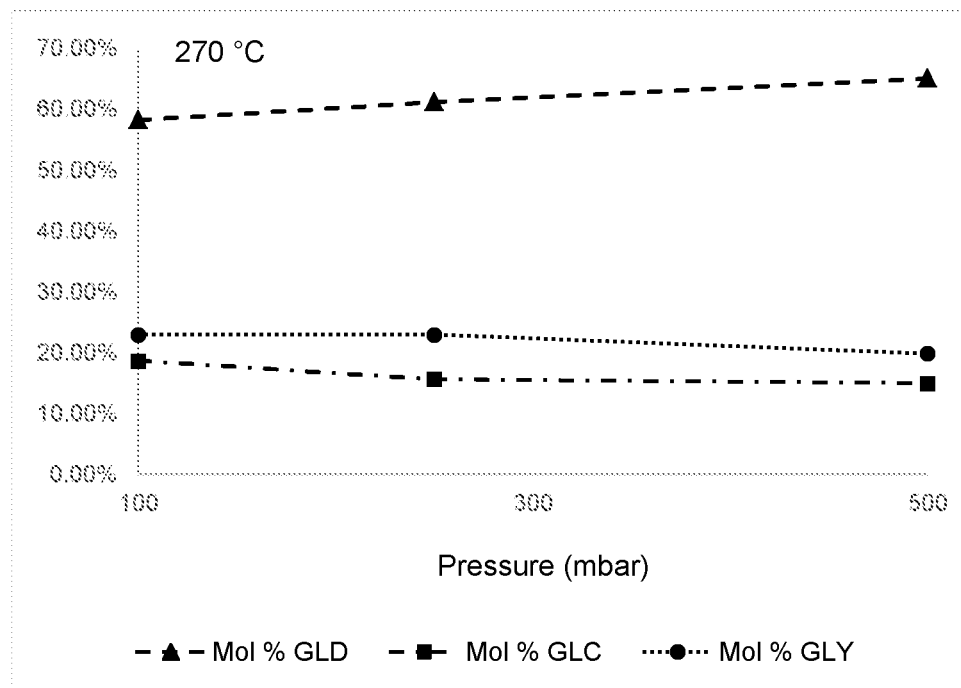
Figure 8:
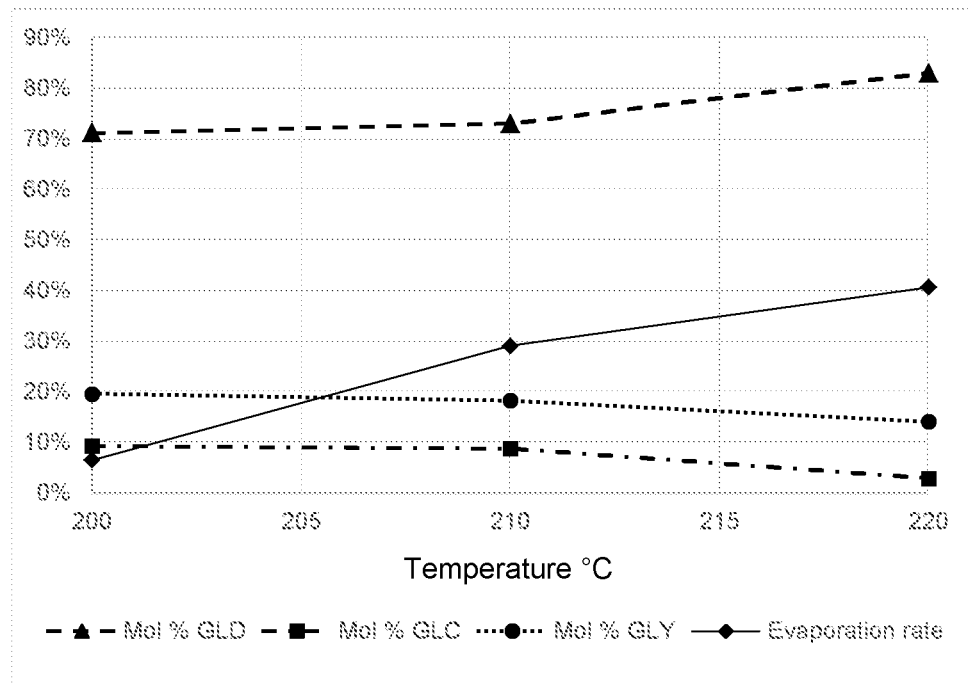
Figure 9:
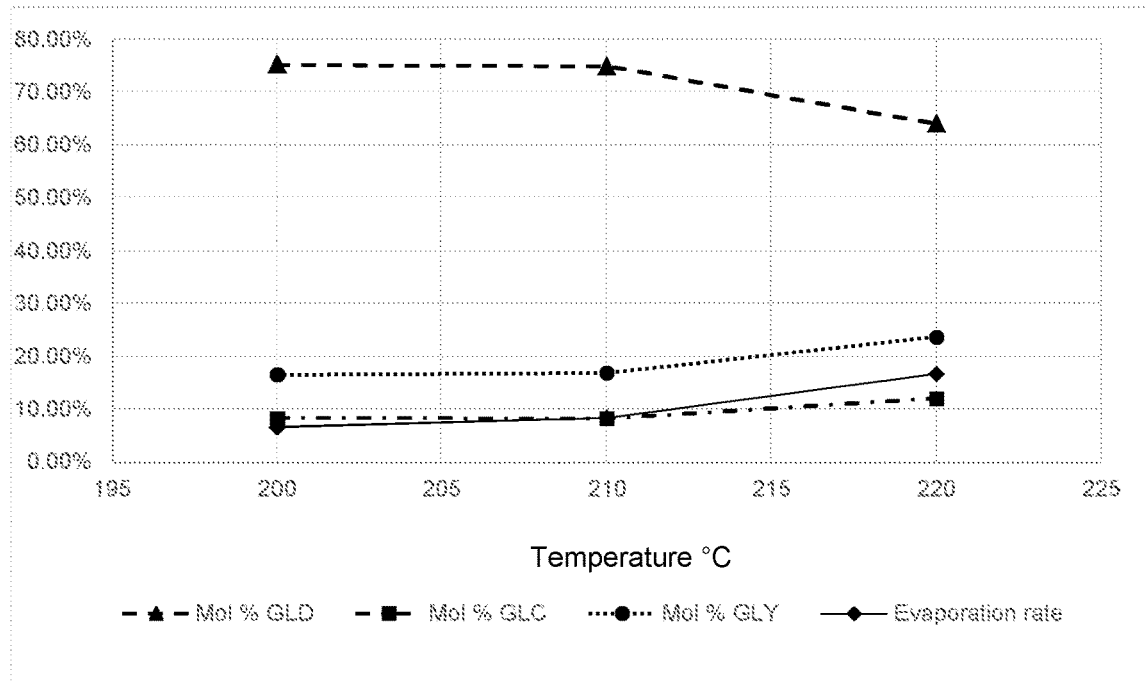
Figure 10:
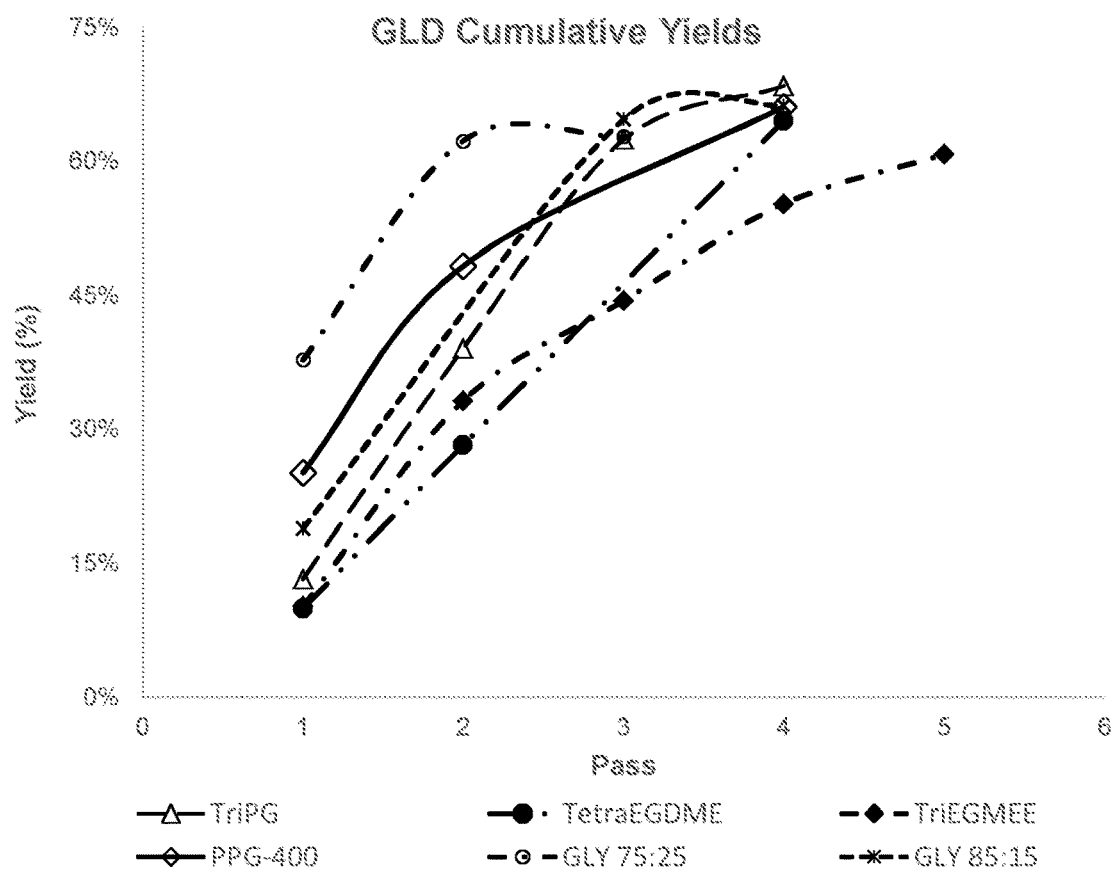

The invention will now be described with reference to the following Examples and Figures wherein:

FIG. 1a: shows hyperbranched aliphatic polyether polyols as a solid by-product;

FIG. 1b: shows an oligomer of glycerol that may be produced as by-product;

FIG. 2: is a schematic diagram illustrating the decarboxylation of GLC to form GLD in accordance with the process of the invention;

FIG. 3: is a graph showing the compositional analysis of the distillate formed during thermal decarboxylation of GLC in the presence of decarboxylation promotor (GLY) in an evaporator operated at 230° C. and at 100 mbar over time;

FIG. 4: is a graph showing the compositional analysis of the distillate formed during thermal decarboxylation of GLC in the presence of decarboxylation promotor (GLY) in an evaporator operated at 270° C. and atmospheric pressure (1013 mbar) over time;

FIG. 5: is a graph showing the compositional analysis of the distillate formed during thermal decarboxylation of GLC in the presence of decarboxylation promotor (GLY) in an evaporator operated at 230° C. and at various pressures;

FIG. 6: is a graph showing the compositional analysis of the distillate formed during thermal decarboxylation of GLC in the presence of decarboxylation promotor (GLY) in an evaporator operated at 250° C. and at various pressures;

FIG. 7: is a graph showing the compositional analysis of the distillate formed during thermal decarboxylation of GLC in the presence of decarboxylation promotor (GLY) in an evaporator operated at 270° C. and at various pressures;

FIG. 8: is a graph showing the compositional analysis of the distillate formed during thermal decarboxylation of GLC in the presence of decarboxylation promotor (GLY) in an evaporator operated at 100 mbar and at various temperatures;

FIG. 9: is a graph showing the compositional analysis of the distillate formed during thermal decarboxylation of GLC in the presence of decarboxylation promotor (GLY) in an evaporator operated at 500 mbar and at various temperatures; and FIG. 10: is a graph showing cumulative yield of GLD based on the thermal decarboxylation of GLC in the presence of different decarboxylation promotors in an evaporator operated at 230° C. and at 100 mbar over time.

As illustrated in FIG. 2, a mixed liquid glycerol carbonate (GLC) and decarboxylation promotor (DP) feed stream (15) may be pumped (P1), for instance by means of a gear pump, to an agitated thin-film evaporator (E1) for heating and separation of formed glycidol (GLD) by evaporation in accordance with the method of the invention. Prior to feeding into the evaporator (E1), the mixed liquid glycerol carbonate (GLC) and decarboxylation promotor (DP) feed stream (15) may be pre-heated by means of a preheater (H) to produce a preheated mixed feed stream (16). The evaporator (E1) is preferably in the form of a vertical and cylindrical agitated thin-film evaporator with wipers or blades.

Once the heated mixed liquid glycerol carbonate (GLC) and decarboxylation promotor (DP) stream (16) is fed into the evaporator (E1), it is evenly distributed on the inner wall of the evaporator (E1) by the rotating blades/wipers before the thickness of the film grows such that turbulent flow develops, allowing optimum heat flux through the liquid and mass transfer to the vapour phase. For example, in some configurations, the volumetric flow rate of the liquid feed stream is increased so that the thickness of the film on the inner walls of the evaporator (E1) exceeds the thickness of the clearance between the blades/wipers and the inner wall of the evaporator (E1), the movement of the blades/wipers creates a fillet/bow wave in the film, giving rise to turbulent flow.

The glycerol carbonate (GLC) fed into the evaporator (E1) undergoes thermal decaboxylation in the presence of the decarboxylation promotor to form glycidol (GLD) and carbon dioxide. The glycidol (GLD) formed rapidly evaporates to the gas phase and is extracted counter-currently or co-currently to the liquid entering the evaporator (E1) under reduced pressure, provided by vacuum pump (V). In alternative configurations to that illustrated in FIG. 6, evaporated glycidol (GLD) may be forced out of the evaporator (E1) using an inert carrier gas (for example, nitrogen). A liquid effluent stream (17) is also extracted from the evaporator (E1) which comprises non-volatile material and unreacted glycerol carbonate (GLC), which may be collected in a collector vessel (107). The unreacted glycerol carbonate (GLC) in the collector vessel (107) may be recycled to the liquid glycerol carbonate feed stream (15) by means of a pump (P2), which is preferably a gear pump.

A gaseous glycidol (GLD) effluent stream (18) from the evaporator (E1) is subsequently passed to a condenser (108) which condenses condensable vapours, primarily glycidol product, to form a mixed gas-liquid stream (19) which is subsequently fed to a gas-liquid separator (109). The gaseous portion, which is primarily carbon dioxide, is withdrawn as stream (20) from the separator (109) and is passed through a cold condensation trap (111) which condenses any remaining condensable vapours which may be detrimental to the vacuum pump (V) located downstream. The carbon dioxide waste stream (22) may subsequently be conveyed to downstream processes for capture and appropriate disposal.

A liquid stream (21) corresponding to a crude glycidol product is withdrawn from the separator (109) and is stored in vessel (110). The crude glycidol product in vessel (110) may be passed on to a distillation column or to another agitated thin-film evaporator for further purification. Any glycerol carbonate (GLC) or decarboxylation promotor impurity isolated following purification may also be recycled back to the feed stream (15).

EXAMPLES

Stream Analysis

The distillate stream was analysed by $^1$H NMR spectroscopy while the residue was analysed by HPLC using a refractive index detector. NMR solvent used was $D_6$-DMSO, with acetonitrile internal standard. The stationary phase used for the HPLC was an organic acids column (Phenomenex Rezex ROA—Organic Acids H+), the mobile phase was 7.5% acetonitrile, 0.5 mM aqueous $H_2SO_4$ and ethylene glycol was employed as an internal standard.

Example 1

Thermal Decarboxylation with Wiped Film Evaporator and Recycle of Residue

A UIC DSL-5 wiped film glass evaporator was heated to a temperature of 230° C. using stainless steel band clamp heaters and connected, by means of a counter-current outlet, to a vacuum pump which was operated to maintain the system at a pressure of 100 mbar and a cold trap was placed before the vacuum pump to eliminate product loss. A residue outlet of the evaporator was equipped with a gear pump and a back pressure regulator so as to remove residue liquid from the bottom of the evaporator whilst the vapour outlet at the top of the evaporator connected to a coiled condenser and a receiver vessel to which vapours from the evaporator were fed, counter-currently to the liquid feed. The receiver vessel also included an outlet gear pump and back pressure regulator valve.

Decarboxylation promotor (GLY) and GLC (3.3 kg) were mixed in a molar ratio of 75:25 and fed from a feeding vessel to the top the evaporator at an approximate rate of 1.2 kg/h using a pump and the rotor speed of the evaporator was set to 400 RPM. Continuous recycle of residue in the residue collector vessel to the feeding vessel was employed by pumping directly from the residue collector vessel to the feeding vessel for the evaporator using a gear pump. A separate supply of decarboxylation promotor (GLY) was also continuously added to the feeding vessel, at a rate of 180 g/h, to accommodate for loss of decarboxylation promotor from the evaporator through evaporation.

The composition of the distillate obtained in the receiver vessel was repeatedly measured over the course of the experiment, the results of which are shown in FIG. 3. The results show that a glycidol concentration of approximately 60 mol. % was maintained over the course of the experiment, with the remaining components being unreacted GLC and decarboxylation promotor (GLY) which evaporated from the liquid phase reaction mixture with GLD. No solid by-products were formed in the evaporator and an overall yield of glycidol based on converted GLC was 73.9%, without the use of a catalyst.

Example 2

Thermal Decarboxylation with Wiped Film Evaporator and Recycle of Residue

The experiment according to Example 1 was repeated, except that the evaporator was heated to a temperature of 270° C. and operated at atmospheric pressure (1013 mbar) and the rate of supplemental decarboxylation promotor (GLY) addition to the feeding vessel was at a rate of 120 g/h, to accommodate for loss of decarboxylation promotor from the evaporator through evaporation.

The composition of the distillate obtained in the receiver vessel was repeatedly measured over the course of the experiment, as in Example 1, and the results of which are shown in FIG. 4. The results show that a glycidol concentration of approximately 80 mol. % was maintained over the course of the experiment, with only minor amounts of unreacted GLC and decarboxylation promotor (GLY) contained in the distillate. FIG. 4 also shows the evaporation rate in the evaporator as a fraction of the total feed. As can be seen, the evaporation rate slowly rises and falls over the course of the experiment. One explanation for this observation is that over time the amount of GLC-decarboxylation promotor precursor adduct increases and, as this builds up, the rate of glycidol production and evaporation also increases before reducing as the amount of the adduct reduces following decarboxylation to form GLD.

Example 3

Thermal Decarboxylation with Wiped Film Evaporator without Recycle of Residue

The experiment according to Example 1 was repeated, except that several different combinations of evaporator temperatures (230, 250 and 270° C.) and pressures (100, 250, 350 and 500 mbar) were tested in a series of experiments and without recycle of residue. The composition of the distillate was assessed during each of the different experiments, and after only a single pass through the evaporator, to determine the extent of GLD formation and the degree of evaporation of unreacted GLC and decarboxylation promotor from the liquid phase mixture.

FIGS. 5 to 7 show the results of the distillate compositional analysis for a particular evaporator temperature over the different pressures tested. At each of the evaporator temperatures tested, improvement in GLD yield is seen from increasing the pressure of the evaporator from 100 mbar to 500 mbar. The results also show that at lower temperatures, the rate of distillation of decarboxylation promotor (GLY) and GLC is more sensitive to pressure than at higher temperatures. For example, at an evaporator temperature of 230° C. (FIG. 5) the amount of decarboxylation promotor (GLY) which is distilled decreases from 27% to 7% upon increasing the pressure from 100 to 500 mbar.

In contrast, at an evaporator temperature of 270° C. (FIG. 7), the amount of decarboxylation promotor (GLY) which is distilled decreases by only 3% across the same pressure range. It was also observed that at an evaporator temperature of 270° C. the evaporation rate was very high where low pressures evaporator pressures of 100 to 250 mbar were also used and some undesired by-product solids formation in the evaporator was noted.

The evaporation rate for experiments with evaporator temperatures of 230° C. and 250° C. (FIGS. 5 and 6) was also recorded during those experiments and a general decrease in evaporation rate may be seen as the pressure of the system is increased. For example, at 230° C. the evaporation rate decreases from 12 to 6% going from 100 to 500 mbar. Analysis of the residues showed that there was between 10 and 15 mol. % GLD in the residue indicating that under these conditions not all of the GLD formed in the liquid film was evaporated. This can be attributed to: i) a temperature gradient existing down the length of the evaporator, resulting in a higher rate of GLD production towards the bottom of the evaporator, where there is insufficient time for evaporation before extraction with the residue liquid; and ii) mass transfer limitations to evaporation as a result of the presence of decarboxylation promotor and by-products in the liquid film.

These experiments show that a good level of GLD yield is achievable over a wide range of temperatures and pressures and that system conditions can be readily modified to improve yield of GLD further. As these experiments were conducted with only a single pass through the evaporator, yields would also be expected to be further enhanced by including residue recycle. A larger amount of decarboxylation of the GLC-decarboxylation promotor adduct formed is typically observed in the second "pass" through the evaporator.

Example 4

Thermal Decarboxylation with Wiped Film Evaporator and Lowered Feed Rate

The experiment according to Example 1 was repeated, except that several different combinations of evaporator temperatures (200, 210 and 220° C.) and pressures (100 and 500 mbar) were tested in a series of experiments, the feed flow rate was lowered to 0.3 kg/h and experiments performed without recycle of residue. The composition of the distillate was assessed, after only one "pass" through the evaporator, during each of the different experiments to determine the extent of GLD formation and the degree of evaporation of unreacted GLC and decarboxylation promotor from the liquid phase mixture.

FIGS. 8 and 9 show the results of the distillate compositional analysis for a particular evaporator pressure (100 mbar and 500 mbar, respectively) over the different temperatures tested, after only one "pass" through the evaporator. Unwanted GLC evaporation was substantially reduced in these experiments. By changing the temperature of the evaporator from 230° C. (Example 3) to 220° C. and the feed flow rate from 1.2 kg/h (Example 3) to 0.3 kg/h the composition of GLC in the distillate was reduced from 12 to 3 mol %. These experiments therefore show that a good level of GLD yield is achievable over different feed flow rates and evaporator temperatures and that system conditions can be readily modified to improve yield of GLD further.

Example 5

Batch Process with Wiped Film Evaporator and Recycle of Residue Using Different Decarboxylation Promotors The experiment according to Example 1 was repeated, except that several different decarboxylation promotors were mixed in a 75:25 molar ratio (GLC : Decarboxylation Promotor) and the GLC source contained 5 mol. % of glycerol contaminant. Additionally, the condensate residue from the evaporator was collected following each pass of all of the GLC reactant from the feed vessel through the evaporator before being recycled back to the feed vessel for further "passes" throught the evaporator until such time as either no further distillate was collected or solids formation in the evaporator was evident. A further experiment was also conducted in which the amount of decarboxylation promotor (GLY) in the initial liquid phase reaction was reduced to 15 mol. % (GLC:GLY, 85:15). The results are provided in Table 1 below and in FIG. 10.

Some solids formation was noticeable with polyethylene glycol-400 and polypropylene glycol-400. This may be attributed to the higher molecular weight of these decarboxlation promotors and such solids formation may be reduced by adopting a low evaporation rate.

TABLE 1

| Decarboxylation Promotor | Total Passes | GLD Yield | Total Decarboxylation Promotor stripped to distillate | Solids Formation |
|---|---|---|---|---|
| Tripropylene glycol | 4 | 68.4% | 84.6% | No |
| Tetraethylene glycol | 7 | 66.4% | 8.5% | No |
| Triethleneglycol monoethylether | 5 | 60.7% | 97.6% | No |
| Polyethylene glycol-400 | 2 | 49.0% | 5.4% | Yes |
| Polypropylene glycol-400 | 5 | 65.9% | 3.8% | Yes |
| Glycerol (75:25) | 3 | 62.7% | 26.9% | No |
| Glycerol (85:15) | 4 | 66.2% | 31.3% | No |

The above results show that the different decarboxylation promotors according to the invention are capable of providing similar overall GLD yields, in the absence of any catalyst. Changing the composition of the liquid phase mixture to reduce the amount of decarboxylation promotor ("Glycerol (75:25)" vs Glycerol (85:15)") therein is shown in FIG. 10 to lead to a reduction in the initial rate of GLD formation. However, a similar overall GLD yield is shown to nevertheless be achieved, albeit over a greater number of "passes" through the evaporator.

The invention claimed is:

1. A process for the preparation of glycidol by thermal decarboxylation of glycerol carbonate, said process comprising the steps of:
   a) contacting liquid glycerol carbonate with a decarboxylation promotor, having a boiling point of at least 160° C. at atmospheric pressure and consisting essentially of an aliphatic mono-ol, an aliphatic polyol, or mixtures thereof, to form a liquid phase mixture;
   b) applying heat to the liquid phase mixture formed in step a) to induce thermal decarboxylation of the glycerol carbonate; and
   c) separating glycidol formed in step b) from the liquid phase mixture by evaporation of glycidol; and
   wherein the process does not comprise the use of a decarboxylation catalyst.

2. A process according to claim 1, wherein the mono-ol and/or polyol is acyclic and comprises one or more ether groups, or a mono-ol and/or polyol which has a plurality of ether groups and a primary hydroxyl group.

3. A process according to claim 1, wherein the polyol is selected from polyethylene glycol, polypropylene glycol, and oligomers of ethylene glycol, propylene glycol and glycerol.

4. A process according to claim 1, wherein the polyol is selected from vicinal polyols.

5. A process according to claim 1, wherein the polyol is selected from ethylene glycol, propylene glycol, glycerol, 1,2-butanediol, 2,3-butanediol and erythritol; or wherein the polyol is selected from glycerol and erythritol.

6. A process according to claim 1, wherein the mono-ol is selected from monoethers of polyethylene glycol and polypropylene glycol or monoethers of oligomers of ethylene glycol and propylene glycol.

7. A process according to claim 1, wherein the decarboxylation promotor is or consists of, a mixture of a mono-ol and a polyol.

8. A process according to claim 1, wherein the decarboxylation promotor has a boiling point of at least 180° C., at atmospheric pressure.

9. A process according to claim 1, wherein the decarboxylation promotor is present in the liquid mixture formed in step a) in an amount of from 5 to 70 mol. % based on the combination of glycerol carbonate and decarboxylation promotor.

10. A process according to claim 1, further comprising forming a turbulent film of liquid reaction mixture.

11. A process according to claim 1, wherein the mixture is heated to a temperature of from 125° C. to 300° C.

12. A process according to claim 1, wherein the process is carried out at a pressure of less than or equal to 20.0 kPa absolute (200 mbar absolute).

13. A process according to claim 1, wherein evaporation in step c) is facilitated by a flow of an inert gas.

14. A process according to claim 1, wherein heating in step b) and evaporation of glycidol in step c) is conducted in an evaporator supplied with one or more feeds for introducing liquid glycerol carbonate and the decarboxylation promotor.

15. A process according to claim 14, wherein the evaporator is a falling film evaporator, a rising film evaporator, a rising-falling film evaporator, an agitated thin-film evaporator, a long-tube evaporator, a short-tube evaporator, a batch pan evaporator, a multiple-effect evaporator, a plate-type evaporator, a vapour-compression evaporator or a forced circulation evaporator.

16. A process according to claim 14, wherein a feed comprising liquid glycerol carbonate is preheated prior to being fed into the evaporator.

17. A process according to claim 14, wherein the liquid glycerol carbonate is introduced into the evaporator at a rate which is greater than or equal to the rate of evaporation of glycidol formed in the evaporator.

18. A process according to claim 14, wherein an oligomer of glycerol is formed as minor by-product of the process, and the process further comprises using the by-product oligomer of glycerol as a decarboxylation promotor in the process.

19. A process according to claim 14, wherein the process further comprises recycling recovered unreacted glycerol carbonate and/or decarboxylation promotor and/or directing by-product oligomer of glycerol to the feed(s) to the evaporator.

20. A process for the preparation of glycidol by thermal decarboxylation of glycerol carbonate, said process comprising the steps of:
   a) contacting liquid glycerol carbonate with a decarboxylation promotor, having a boiling point of at least 160° C. at atmospheric pressure and consisting essentially of a mono-ol, optionally in combination with an aliphatic polyol, to form a liquid phase mixture, wherein the mono-ol is a phenyl substituted $C_1$ to $C_6$, linear or branched chain, alkylhydroxy group;
   b) applying heat to the liquid phase mixture formed in step a) to induce thermal decarboxylation of the glycerol carbonate; and
   c) separating glycidol formed in step b) from the liquid phase mixture by evaporation of glycidol; and
   wherein the process does not comprise the use of a decarboxylation catalyst.

21. A process according to claim 20, wherein poly-ol is present in combination with the mono-ol.

22. A process according to claim 20, wherein the hydroxyl group of the mono-ol is a primary alcohol.

* * * * *

UNITED STATES PATENT AND TRADEMARK OFFICE
CERTIFICATE OF CORRECTION

| | | |
|---|---|---|
| PATENT NO. | : 11,472,783 B2 | Page 1 of 1 |
| APPLICATION NO. | : 17/042309 | |
| DATED | : October 18, 2022 | |
| INVENTOR(S) | : Atkins et al. | |

It is certified that error appears in the above-identified patent and that said Letters Patent is hereby corrected as shown below:

On the Title Page

Column 1, Item (30):
"Foreign Application Priority Data: Mar. 28, 2018 (GB)... 1805029"

Should Read:
--Foreign Application Priority Data: Mar. 28, 2018 (GB)... 1805029.4--

Signed and Sealed this
Twenty-seventh Day of December, 2022

Katherine Kelly Vidal
*Director of the United States Patent and Trademark Office*